United States Patent
Schmülling et al.

(10) Patent No.: US 9,127,073 B2
(45) Date of Patent: Sep. 8, 2015

(54) ROCK2 AND ROCK3, TWO NEW GAIN-OF-FUNCTION VARIANTS OF THE CYTOKININ RECEPTORS AHK2 AND AHK3

(75) Inventors: Thomas Schmülling, Berlin (DE); Tomás Werner, Berlin (DE); Isabel Bartrina y Manns, Berlin (DE); Helen Braun, Berlin (DE)

(73) Assignee: Freie Universitat Berlin, Berlin (DE)

( * ) Notice: Subject to any disclaimer, the term of this patent is extended or adjusted under 35 U.S.C. 154(b) by 0 days.

(21) Appl. No.: 13/382,922

(22) PCT Filed: Jul. 9, 2010

(86) PCT No.: PCT/EP2010/059885
§ 371 (c)(1),
(2), (4) Date: Jan. 7, 2012

(87) PCT Pub. No.: WO2011/004005
PCT Pub. Date: Jan. 13, 2011

(65) Prior Publication Data
US 2012/0272409 A1    Oct. 25, 2012

(30) Foreign Application Priority Data
Jul. 10, 2009 (EP) ..................................... 09165161

(51) Int. Cl.
| | | |
|---|---|---|
| C12N 15/00 | (2006.01) | |
| C12N 5/04 | (2006.01) | |
| C12N 5/10 | (2006.01) | |
| C07H 21/04 | (2006.01) | |
| C07K 14/00 | (2006.01) | |
| C12N 15/82 | (2006.01) | |
| C12N 15/87 | (2006.01) | |
| A01H 5/00 | (2006.01) | |
| C07K 14/415 | (2006.01) | |

(52) U.S. Cl.
CPC .......... *C07K 14/415* (2013.01); *C12N 15/8261* (2013.01); *C12N 15/8295* (2013.01)

(58) Field of Classification Search
USPC ....................................................... 800/283
See application file for complete search history.

(56) References Cited

U.S. PATENT DOCUMENTS

2002/0177162 A1* 11/2002 Kakimoto et al. ............. 435/7.1

FOREIGN PATENT DOCUMENTS

| WO | WO 2004/108931 | 12/2004 |
|---|---|---|
| WO | WO 2007/003317 | 1/2007 |
| WO | WO 2007/137810 | 12/2007 |

OTHER PUBLICATIONS

Ferreira et al, Cytokinin signaling, Curr. Opin. Plant Biol. (2005) 8:518-525.*
Miwa Kumiko et al, Identification of amino acid substitutions that render the *Arabidopsis* cytokinin receptor histidine kinase AHK4 constitutively active, Plant and Cell Physiol. (2007) 48:1809-1814.*
Kim Hyo Jung et al., Cytokinin-mediated control of leaf longevity by AHK3 through phosphorylation of ARR2 in *Arabidopsis*, Proc. Natl Acad. Sci. (2006) 103:814-819.*
Grantham, R., Amino acid difference formula to help explain protein evolution, Science (1974) 185:862-864.*
Friedberg I., Automated Protein Function Prediction—The Genomic Challenge, Brief. Bioinformatics (2006) 7:225-242.*
Yamada et al, The *Arabidopsis* AHK4 histidine kinase is a cytokinine-binding receptor that transduces cytokinin signals across the membrane, Plant Cell Physiol. (2001) 42:1017-1023.*
Miwa Kumiko et al, Identification of amino acid substitutions that render the *Arabidopsis* cytokinin receptor histidine kinase AHK4 constitutively active, *Plant and Cell Physiology*, vol. 48, NR. 12, pp. 1809-1814 (2007).
Werner et al, Cytokinin-deficient transgenic *Arabidopsis* plants show multiple developmental alterations indicating opposite functions of cytokinins in the regulation of shoot and root meristem activity, *Plant Cell, American Society of Plant Physiologists*, vol. 15, No. 11, pp. 2532-2550 (2003).
Higuchi Masayuki et al, In planta functions of the *Arabidopsis* cytokinin receptor family, *Proceedings of the National Academy of Sciences of USA, National Academy of Science*, vol. 101, No. 23, (2004).
Kim Hyo Jung et al., Cytokinin-mediated control of leaf longevity by AHK3 through phosphorylation of ARR2 in *Arabidopsis, Proceedings of the National Academy of Sciences of the USA*, vol. 103, Nr. 3, (2006).

* cited by examiner

*Primary Examiner* — Cathy Kingdon Worley
*Assistant Examiner* — Mykola Kovalenko
(74) *Attorney, Agent, or Firm* — VLP Law Group LLP; Kent H. Cheng

(57) ABSTRACT

The present invention relates to two new gain of function variants of the cytokinin receptor proteins AHK2 and AHK3, namely rock2 and rock3, to transgenic organisms comprising at least one of said new gain-of-function cytokinin receptor variants and to a method for the manufacturing of a transgenic plant comprising at least one of the new gain-of-function variants.

29 Claims, 5 Drawing Sheets

A.

B.

ROCK2 AND ROCK3, TWO NEW GAIN-OF-FUNCTION VARIANTS OF THE CYTOKININ RECEPTORS AHK2 AND AHK3

PRIORITY CLAIM

This is a U.S. national stage of application No. PCT/EP2010/059885, filed on Jul. 9, 2010. Priority is claimed on the following application: EP Application No.: 09165161.2 filed on Jul. 10, 2009, the contents of which are incorporated here by reference.

SEQUENCE LISTING

The instant application contains a Sequence Listing which has been submitted in ASCII format via EFS-Web and is hereby incorporated by reference in its entirety. Said ASCII copy, created on Mar. 7, 2012, is named 566126PU.txt and is 32,190 bytes in size.

BACKGROUND OF THE INVENTION

In order to be able to supply a continuously growing population with food and other plant-derived products, people have always been interested in improving the productivity in agriculture.

The productivity of a plant can be influenced in various different ways, e.g. by improving plant growth characteristics or by delaying leaf senescence. There are several mechanisms and pathways known which are involved in plant growth and development.

Cytokinin is a plant hormone that plays positive and negative regulatory roles in many aspects of plant growth and development. It stimulates the formation and activity of shoot meristems, is able to establish sink tissues, retards leaf senescence, inhibits root growth and branching, and it plays a role in seed germination and stress responses. Analysis of cytokinin-deficient plants has shown that cytokinin plays opposite roles in shoot and root meristems and suggests that the hormone has an essential function in quantitative control of organ growth (Mok, D. W. S. & Mok, M. C. (2001) Ann. Rev. Plant Physiol. Mol. Bio. 52, 89-118). For the model plant *Arabidopsis thaliana* it has been shown that the cytokinin signal is perceived by three members of the cytokinin receptor family, which are sensor histidine kinases (Inoue, T. et al. (2001) Nature 409, 1060-3; Suzuki, T. et al. (2001) Plant Cell Physiol. 42, 107-13; Yamada, H. et al. (2001) Plant Cell Physiol. 42, 1017-23.). These three cytokinin receptors, AHK2, AHK3 and CRE1/AHK4, show a high degree of sequence identity, but each has distinguishing characteristics.

Recently, a gain-of-function variant of the cytokinin receptor AHK3 has been disclosed and called ore12 (see WO 2007/108931 A1). It was shown that ore12 expression in *Arabidopsis thaliana* yields plants with delayed leaf senescence, whereas the overall appearance of the whole plant showed no significant difference compared to wild type plants. Although expression of ore12 may lead to plants with delayed leaf senescence and thereby to plants with improved productivity, ore12 expression had no significant effect on other plant growth characteristics. Thus, there remains a need for further improvement of plant productivity.

It is an object of the present invention to provide means and methods suitable to produce transgenic plants with improved productivity and/or growth characteristics.

SUMMARY OF THE INVENTION

This object is achieved by the present invention as set out in detail below.

The present invention provides two novel gain-of-function variants of the cytokinin receptors AHK2 and AHK3, namely rock2 and rock3. The rock2 polypeptide with the amino acid sequence SEQ ID No. 1 is a constitutively active variant of the cytokinin receptor AHK2 of *Arabidopsis thaliana* and can be encoded by a nucleic acid with the sequence of SEQ ID No. 3. The rock3 polypeptide with the amino acid sequence SEQ ID No. 2 is a constitutively active variant of the cytokinin receptor AHK3 of *Arabidopsis thaliana* and can be encoded by a nucleic acid with the sequence of SEQ ID No. 4. As used herein, the term "constitutively active variant" of a cytokinin receptor AHK2 or AHK3 preferably refers to a polypeptide that phosphorylates essentially the same target structures as the respective wild type AHK receptor AHK2 or AHK3, but wherein said kinase activity of the constitutively active variant is basically independent from cytokinin binding. Thus, the term "constitutively active variant" also comprises polypeptides that lack any specific binding to cytokinin and polypeptides that may even lack a functional or non-functional cytokinin binding domain. The skilled person is well aware of suitable methods of how to test a given polypeptide for its kinase activity. Preferably the in vitro kinase assay is used as described by Mähönen et al. in "Cytokinins Regulate a Bidirectional Phosphorelay Network in *Arabidopsis*" Current Biology (2006), 16, 1116-1122. In a particular preferred embodiment, the constitutively active variant exhibits at least 30% of the kinase activity of the respective wild type AHK receptor AHK2 or AHK 3, more preferably at least 50% of the kinase activity of AHK2 or AHK3, respectively.

It was surprisingly found that transgenic expression of a polypeptide comprising an amino acid sequence with the SEQ ID Nos. 1 or 2 leads to transgenic plants exhibiting improved growth characteristics and delayed leaf senescence. The effect of transgenic expression of an amino acid sequence with the SEQ ID Nos. 1 or 2 in a plant on leaf senescence is more pronounced than that already observed for the known gain-of-function variant of AHK3, ore12. Even more surprisingly, it was found for the first time that transgenic expression of the AHK2 or AHK3 gain-of-function variant of an amino acid sequence with the SEQ ID Nos. 1 or 2 has a significant effect on shoot growth, number of siliques per main stem, stem thickness and/or flower size of the resulting transgenic plant when compared to wild type, whereas plants expressing ore12 lack such an effect. Thus, transgenic expression of an amino acid sequence with the SEQ ID Nos. 1 or 2 leads to plants exhibiting improved productivity.

In a first aspect of the present invention, an isolated nucleic acid is provided, comprising a nucleic acid sequence encoding for:

i) an amino acid sequence with the SEQ ID No. 1 or an orthologue thereof;

ii) an amino acid sequence having at least 48%, preferably at least 50%, more preferably at least 55% identity over the whole sequence length of SEQ ID No. 1; or iii) an amino acid sequence having at least 50%, preferably at least 53%, more preferably 55% identity over a 50 amino acid sequence segment of SEQ ID No. 1 having the SEQ ID No. 5;

wherein the amino acid sequence has the amino acid phenylalanin (F) at a position corresponding to position 552 of SEQ ID No. 1. SEQ ID No. 5 encompasses the 50 amino acid residues of SEQ ID No. 1 located directly towards the N-terminus of the amino acid phenylalanin (F) at position 552 of SEQ ID No. 1.

The present invention also provides an isolated nucleic acid, comprising a nucleic acid sequence encoding for:
i) an amino acid sequence with the SEQ ID No. 2 or an orthologue thereof;
ii) an amino acid sequence having at least 48%, preferably at least 50%, more preferably at least 55% identity over the whole sequence length of SEQ ID No. 2; or
iii) an amino acid sequence having at least 50%, preferably at least 55%, more preferably 60% identity over a 50 amino acid sequence segment of SEQ ID No. 2 having the SEQ ID No. 6;
wherein the amino acid sequence has the amino acid isoleucine (I) at a position corresponding to position 179 of SEQ ID No. 2. SEQ ID No. 6 encompasses the 50 amino acid residues of SEQ ID No. 2 located directly towards the C-terminus of the amino acid isoleucine (I) at position 179 of SEQ ID No. 2.

Preferably an isolated nucleic acid is provided, comprising a nucleic acid sequence encoding at least one of the amino acid sequences with the SEQ ID Nos. 1 or 2 or an orthologue thereof. The term "orthologue" as used herein refers to a nucleic acid or amino acid sequence from a species, preferably different from *Arabidopsis thaliana*, that shows highest similarity, preferably highest sequence identity, to the specified nucleic acid or amino acid sequence of *Arabidopsis thaliana* because both genes originated from a common ancestor. The present invention also provides an isolated polypeptide encoded by an isolated nucleic acid of the invention, preferably an isolated polypeptide comprising at least one of the amino acid sequences with the SEQ ID No. 1 or 2.

In a second aspect the invention provides a transgenic expression cassette for the expression of nucleic acids, wherein the transgenic expression cassette of the invention comprises an isolated nucleic acid according to the present invention. The transgenic expression cassette of the invention may be designed such that it mediates the transgenic expression of the nucleic acid sequence encoding at least one of the amino acid sequences with the SEQ ID No. 1 or 2 in a plant tissue under the control of the at least one promoter in a host organism, preferably a plant cell.

In a third aspect of the invention, a vector is provided comprising an isolated nucleic acid according to the invention or a transgenic expression cassette of the invention.

In a fourth aspect, the present invention is directed to a transgenic organism comprising an isolated nucleic acid according to the invention, a transgenic expression cassette of the invention or a vector of the present invention.

The present invention provides an isolated polypeptide comprising:
A) i) an amino acid sequence with the SEQ ID No. 1 or an orthologue thereof;
ii) an amino acid sequence having at least 48%, preferably at least 50%, more preferably at least 55% identity over the whole sequence length of SEQ ID No. 1; or
iii) an amino acid sequence having at least 50%, preferably at least 53%, more preferably 55% identity over a 50 amino acid sequence segment of SEQ ID No. 1 having the SEQ ID No. 5;
wherein the amino acid sequence has the amino acid phenylalanin (F) at a position corresponding to position 552 of SEQ ID No. 1;
or
B) i) an amino acid sequence with the SEQ ID No. 2 or an orthologue thereof;
ii) an amino acid sequence having at least 48%, preferably at least 50%, more preferably at least 55% identity over the whole sequence length of SEQ ID No. 2; or
iii) an amino acid sequence having at least 50%, preferably at least 55%, more preferably 60% identity over a 50 amino acid sequence segment of SEQ ID No. 2 having the SEQ ID No. 6;
wherein the amino acid sequence has the amino acid isoleucine (I) at a position corresponding to position 179 of SEQ ID No. 2.

In a preferred embodiment, the isolated polypeptide of the invention comprises and/or consists of one of the amino acid sequences with the SEQ ID Nos. 1 or 2.

The present invention also relates to an isolated nucleic acid, comprising a nucleic acid sequence encoding for at least one of the amino acid sequences with the SEQ ID Nos. 1 or 2.

An "isolated" nucleic acid is one that is substantially separated from other nucleic acid molecules, which are present in the natural source of the nucleic acid (e.g., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated nucleic acid of the invention can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived. A nucleic acid is also considered isolated if it has been altered by human intervention, or placed in a locus or location that is not its natural site, or if it is introduced into a cell e.g. by agroinfection. Moreover, an "isolated" nucleic acid, such as a cDNA molecule, can be free from some of the other cellular material with which it is naturally associated, or culture medium when produced by recombinant techniques, or chemical precursors or other chemicals when chemically synthesized. Specifically excluded from the definition of "isolated nucleic acid" are: naturally-occurring chromosomes (such as chromosome spreads), genomic libraries, and whole cell genomic DNA or whole cell RNA preparations of naturally occurring sources (including whole cell preparations that are mechanically sheared or enzymatically digested). Nucleic acids and/or polypeptides of the present invention may be provided in isolated form, i.e. purified from their natural environment, preferably in substantially pure or homogeneous form or free or substantially free of nucleic acid or genes of the species of origin other than the desired sequence.

Nucleic acid according to the present invention may include DNA, RNA, mixtures and/or functional substituents thereof, particularly cDNA, genomic DNA and RNA and may be wholly or partially synthetic. The nucleic acids of the invention comprise single stranded or wholly or partially double stranded poly-nucleotide sequences. The term "isolated" encompasses all these possibilities. For the purpose of the present invention, where a DNA sequence is specified, e.g. with reference to a particular SEQ ID No., unless the context requires otherwise, the RNA equivalent, with U substituted for T where it occurs, is encompassed. The nucleic acid of the invention may be produced by any means, including genomic preparations, cDNA preparations, in vitro synthesis, PCR, RT-PCR, and/or in vitro or in vivo transcription.

The isolated nucleic acid of the invention may comprise at least one nucleic acid sequence selected from:

i) one of SEQ ID Nos. 3 or 4 or a reverse complement thereof;

ii) a functionally equivalent sequence or a reverse complement thereof which has at least 70% homology, preferably at least 75% homology, more preferably at least 80% homology with one of the sequences with SEQ ID Nos. 3 or 4 over a coding sequence segment of at least 300 base pairs, preferably over a coding sequence segment of at least 500 base pairs, more preferably over the whole coding sequence length, and which encodes at least for an isolated polypeptide of the invention, preferably for an amino acid sequence with the SEQ ID Nos. 1 or 2; or iii) functionally equivalent sequences or a reverse complement thereof which hybridize under standard conditions with one of the nucleic acid sequences with SEQ ID Nos. 3 or 4 or with a nucleic acid sequences complementary thereto, and which encode at least for an isolated polypeptide of the invention, preferably for an amino acid sequence with the SEQ ID Nos. 1 or 2.

The nucleic acid sequence with the SEQ ID No. 3 encodes for a polypeptide with the amino acid sequence of SEQ ID No. 1, whereas the nucleic acid sequence with the SEQ ID No. 4 encodes for a polypeptide with the amino acid sequence of SEQ ID No. 2.

For the purpose of the present invention the term "functional equivalent sequence" refers to any sequence not identical with one of SEQ ID Nos. 3 or 4 or a reverse complement thereof, and which encodes for at least one of the amino acid sequences with the SEQ ID Nos. 1 or 2. The skilled person is well aware of the degeneracy of the genetic code, allowing for a number of different nucleic acid sequences encoding for the same amino acid sequence and has no difficulties in determining whether a given nucleic acid sequence encodes for at least one of the amino acid sequences with the SEQ ID Nos. 1 or 2.

Methods for preparing functional equivalent sequences or fragments of the invention preferably comprise the introduction of mutations into one of the sequences described by SEQ ID Nos. 3 or 4 or a reverse complement thereof. Mutagenesis may be random, in which case the mutagenized sequences are subsequently screened for their properties by a trial and error procedure. Methods for mutagenesis of nucleic acid sequences are known to the skilled worker and include by way of example the use of oligonucleotides with one or more mutations compared with the region to be mutated (e.g. in a site-specific mutagenesis). Primers with approximately 15 to approximately 75 nucleotides or more are typically employed, with preferably about 10 to about 25 or more nucleotide residues being located on both sides of the sequence to be modified. Details and procedure for said mutagenesis methods are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treating for example transgenic expression vectors comprising one of the nucleic acid sequences of the invention with mutagenizing agents such as hydroxylamine.

The use of functional equivalent sequences may be particularly beneficial in order to comply with a particular codon usage of a selected organism that may be used to transcribe the nucleic acid of the invention and to express the encoded polypeptide comprising or consisting of at least one of the amino acid sequences with the SEQ ID Nos. 1 or 2.

The isolated nucleic acid of the invention may comprise at least one nucleic acid sequence selected from functionally equivalent sequences or a reverse complement thereof which have at least 80% homology, preferably at least 90% homology, more preferably at least 95% homology with one of the sequence of SEQ ID Nos. 3 or 4 over a coding sequence segment of at least 300 base pairs, preferably over a coding sequence segment of at least 500 base pairs, more preferably over the whole coding sequence length, and which encode at least for an amino acid sequence with the SEQ ID No. 1 or 2.

Homology or identity between two nucleic acid sequences is understood as meaning the identity of the respective sequences over a given sequence length in each case, which is calculated by comparison with the aid of the GAP program algorithm (Wisconsin Package Version 10.0, University of Wisconsin, Genetics Computer Group (GCG), Madison, USA), setting the following parameters:

Gap Weight: 12
Length Weight: 4
Average Match: 2.912
Average Mismatch: −2.003

For example, a sequence which has at least 70% homology or identity with one of the sequences of SEQ ID NO: 3 or 4 on nucleic acid basis is understood as meaning a sequence which, upon comparison with the sequence SEQ ID Nos. 3 or 4 by the above program algorithm with the above set of parameters, has at least 70% homology.

Identity or homology between two amino acid sequences is understood as meaning the identity of the respective sequences over a given sequence length in each case, which is calculated by comparison with the aid of the ClusatW_Bioedit algorithm (Thompson J D et al. (1994) Nucleic Acids Res 22:4673-4680) using default settings in software package Bioedit.

For example, a sequence which has at least 48% homology or identity with one of the sequences of SEQ ID Nos. 1 or 2 on amino acid basis is understood as meaning a sequence which, upon comparison with one of the sequences SEQ ID Nos. 1 or 2 by the above program algorithm with the above set of parameters, has at least 48% identity.

The isolated nucleic acid of the invention may comprise at least one nucleic acid sequence selected from functionally equivalent sequences or a reverse complement thereof which hybridize under standard conditions with one of the nucleic acid sequences with SEQ ID No. 3 or 4 or with a nucleic acid sequences complementary thereto, and which encode at least for an isolated polypeptide of the invention, preferably for an amino acid sequence with the SEQ ID No. 1 or 2.

The term "standard hybridization conditions" is to be understood broadly and means both stringent and/or less stringent hybridization conditions. Such hybridization conditions are described inter alia in Sambrook J, Fritsch E F, Maniatis T et al., in Molecular Cloning—A Laboratory Manual, $2^{nd}$ edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the washing step(s) can be selected from the range of conditions limited by those of low stringency (with approximately 2*SSC at 50° C.) and of high stringency (with approximately 0.2*SSC at 50° C., preferably at 65° C.) (20*SSC: 0.3 M sodium citrate, 3 M NaCl, pH 7.0). In addition, the temperature during the washing step can be raised from low-stringency conditions at room temperature, approximately 22° C., to more stringent conditions at approximately 65° C. Both parameters, the salt concentration and the temperature, can be varied simultaneously, and it is also possible for one of the two parameters to be kept constant and only the other to be varied. It is also possible to employ denaturing agents such as, for example, formamide or SDS during the hybridization. Hybridization in the presence of 50% formamide is preferably carried out at 42° C. Some exemplary conditions for hybridization and washing steps are given below:

(1) Hybridization Conditions with for Example
   a) 4*SSC at 65° C., or
   b) 6*SSC, 0.5% SDS, 100 µg/ml denatured fragmented salmon sperm DNA at 65° C., or
   c) 4*SSC, 50% formamide, at 42° C., or
   d) 2* or 4*SSC at 50° C. (low-stringency condition), or
   e) 2* or 4*SSC, 30 to 40% formamide at 42° C. (low-stringency condition), or
   f) 6*SSC at 45° C., or,
   g) 0.05 M sodium phosphate buffer pH 7.0, 2 mM EDTA, 1% BSA and 7% SDS.

(2) Washing Steps with for Example
   a) 0.1*SSC at 65° C., or
   b) 0.1*SSC, 0.5% SDS at 68° C., or
   c) 0.1*SSC, 0.5% SDS, 50% formamide at 42° C., or
   d) 0.2*SSC, 0.1% SDS at 42° C., or
   e) 2*SSC at 65° C. (low-stringency condition), or
   f) 40 mM sodium phosphate buffer pH 7.0, 1% SDS, 2 mM EDTA.

The isolated nucleic acid of the invention may comprise at least one promoter sequence which may be located upstream in 5'-position to the nucleic acid sequence encode at least for an isolated polypeptide of the invention, preferably for an amino acid sequence with the SEQ ID No. 1 or 2.

A promoter sequence is a nucleic acid sequence which is capable of facilitating or enhancing the transcription of a particular gene. Reference herein to a "promoter" is to be taken in its broadest sense and context and includes the transcriptional regulatory sequences derived from a classical eukaryotic genomic gene, including the TATA box which is required for accurate transcription initiation, with or without a CCAAT box sequence and additional regulatory or control elements (e.g. upstream activating sequences, repressors, enhancers and silencers) which alter gene expression in response to developmental and/or external stimuli, or in a tissue-specific manner.

The term "promoter" may also include the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ. Promoters may contain additional copies of one or more specific regulatory elements, to further enhance expression and/or to alter the spatial expression and/or temporal expression of a nucleic acid molecule to which it is functionally linked. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. The terms "plant-operative" and "operative in a plant" when used herein, in respect of a promoter sequence, shall be taken to be equivalent to a plant-expressible promoter sequence.

Regulatable promoters as part of a binary viral plant expression system are also known to the skilled artisan (Yadav 1999—WO 99/22003; Yadav 2000—WO 00/17365). In the present context, a "regulatable promoter sequence" is a promoter that is capable of conferring expression of a gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression of a gene to which it is functionally linked in a particular location within the plant or alternatively, throughout the plant under a specific set of conditions, such as following induction of gene expression by a chemical compound or other elicitor. Preferably, the regulatable promoter used in the performance of the present invention confers expression in a specific location within the plant, either constitutively or following induction, however, not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon). Similarly, the term "tissue-specific" shall be taken to indicate that expression is predominantly in a particular tissue or tissue-type, preferably of plant origin, albeit not necessarily exclusively in said tissue or tissue-type. Similarly, the term "organ-specific" shall be taken to indicate that expression is predominantly in a particular organ, preferably of plant origin, albeit not necessarily exclusively in said organ. Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin. Those skilled in the art will be aware that an "inducible promoter" is a promoter the transcriptional activity of which is increased or induced in response to a developmental, chemical, environmental, or physical stimulus. Similarly, the skilled artisan will understand that a "constitutive promoter" is a promoter that is transcriptionally active throughout most, but not necessarily all parts of an organism, preferably a plant, during most, but not necessarily all phases of its growth and development. Those skilled in the art will readily be capable of selecting appropriate promoter sequences for use in regulating appropriate expression of the cytokinin receptor protein variants from publicly-available sources, without undue experimentation.

Placing a nucleic acid molecule under the regulatory control of a promoter sequence, or in functional connection or linkage with a promoter sequence, means positioning said nucleic acid molecule such that expression is at least in part controlled by the promoter sequence. A promoter is usually, but not necessarily, positioned upstream, or at the 5'-end, and within 2 kb of the start site of transcription, of the nucleic acid molecule which it regulates, albeit enhancers and silencers, which are also comprised by the term "promoter" may be placed further away from the transcriptional start site. It is thought that these elements bind to proteins capable of long range action due to looping out of the intervening sequence. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

According to the present invention any promoter sequence can be used to produce an isolated nucleic acid of the invention. Preferably the promoter sequence is located upstream of the nucleic acid sequence encode at least for an isolated polypeptide of the invention, preferably for an amino acid sequence with the SEQ ID Nos. 1 or 2. Preferably promoter sequences are used that are active in at least one tissue or cell type of a plant and/or that are active in a microorganism. In order to serve its purpose, the at least one promoter sequence and the nucleic acid sequence encoding at least for an isolated polypeptide of the invention, preferably for an amino acid sequence with the SEQ ID Nos. 1 or 2; are functionally linked with one another.

The present invention refers to an isolated nucleic acid of the invention, further comprising at least one promoter sequence, wherein the at least one promoter sequence and the nucleic acid sequence encoding at least for an isolated polypeptide of the invention, preferably for an amino acid sequence with the SEQ ID Nos. 1 or 2, are functionally linked with one another.

The present invention also refers to an isolated nucleic acid of the invention, further comprising at least one promoter sequence, wherein the nucleic acid sequence encoding at least for an isolated polypeptide of the invention, preferably for an amino acid sequence with the SEQ ID Nos. 1 or 2, is located in 3'-position to the at least one promoter and wherein the at least one promoter sequence and the nucleic acid sequence are functionally linked with one another.

As used herein "functional linkage" means, for example, the sequential arrangement of at least one promoter, of the nucleic acid sequence encoding at least for an isolated polypeptide of the invention, preferably for an amino acid sequence with the SEQ ID Nos. 1 or 2, and, if appropriate, of further regulatory elements such as e.g. a terminator, in such a way that each of the regulatory elements is able to fulfil its expected function in the transgenic expression of the nucleic acid sequence encoding at least for an isolated polypeptide of the invention, preferably for an amino acid sequence with the SEQ ID Nos. 1 or 2. This does not necessarily require a direct linkage in a chemical sense. Genetic control sequences such as, for example, enhancer sequences, can also exert their function on the target sequence from positions which are further remote, or indeed from other DNA molecules. Preferably in the isolated nucleic acid of the invention, the nucleic acid sequence encoding at least for an isolated polypeptide of the invention, preferably for an amino acid sequence with the SEQ ID Nos. 1 or 2 is positioned downstream of the sequence which acts as the at least one promoter sequence so that both sequences are coupled covalently with one another. Preferably, the distance between the at least one promoter sequence and the nucleic acid sequence encoding at least for an isolated polypeptide of the invention, preferably for an amino acid sequence with the SEQ ID Nos. 1 or 2 is less than 200 base pairs, especially preferably less than 100 base pairs, very especially preferably less than 50 base pairs. The at least one promoter and the nucleic acid encoding at least for an isolated polypeptide of the invention, preferably for an amino acid sequence with the SEQ ID Nos. 1 or 2 may be selected and functionally linked in such way as to allow for transgenic expression of an isolated polypeptide of the invention, preferably of at least one of the amino acid sequences with the SEQ ID Nos. 1 or 2 in a transgenic organism.

"Expression" means in this context the transcription of the nucleic acid sequence to be expressed transgenically, but can also include the translation of the transcribed RNA of the nucleic acid sequence to be expressed transgenically into a corresponding polypeptide.

"Transgenic" means—for example regarding a transgenic expression cassette, a transgenic expression vector, a transgenic organism or method for the transgenic expression of nucleic acids-all those constructs which are the result of transgenic methods, or all methods using them, in which an isolated nucleic acid of the invention is not located in their natural genetic environment or has been modified by transgenic methods, where the modification can be for example a substitution, addition, deletion, inversion or insertion of one or more nucleotide residues. Preferably, the at least one promoter sequence of the isolated nucleic acid according to the invention is heterologous with regard to the further nucleic acid sequence which is linked functionally with it and which is to be expressed transgenically. In this context, "heterologous" means that the further nucleic acid sequence does not comprise the coding sequence which is naturally under the control of said promoter.

"Natural genetic environment" means the natural chromosomal locus in the organism of origin or the presence in a genomic library. In the case of a genomic library, the natural genetic environment of the nucleic acid sequence is preferably retained at least in part. The environment flanks the nucleic acid sequence at least at one side and has a sequence length of at least 50 bp, preferably at least 500 bp, especially preferably at least 1000 bp, very especially preferably at least 5000 bp. A naturally occurring expression construct becomes a transgenic expression construct when this combination is modified by non-natural, synthetic ("artificial") methods such as, for example, an in-vitro mutagenesis. Such methods have been described (U.S. Pat. No. 5,565,350; WO 00/15815; see also hereinabove).

"Transgenic" with regard to an expression ("transgenic expression") preferably means all those expressions which have been carried out using a transgenic expression cassette, transgenic expression vector or transgenic organism, as defined hereinabove or below.

A functional linkage between the at least one promoter and the nucleic acid sequence to be expressed can be produced by means of conventional recombination and cloning techniques as are described, for example, in Maniatis T et al. (1989) Molecular Cloning: A Laboratory Manual, Cold Spring Harbor Laboratory, Cold Spring Harbor, N.Y. and in Silhavy T J et al. (1984) Experiments with Gene Fusions, Cold Spring Harbor Laboratory, Cold Spring Harbor, N.Y. and in Ausubel F M et al. (1987) Current Protocols in Molecular Biology, Greene Publishing Assoc. and Wiley Interscience. A method which is suitable for this purpose is, for example, the GATEWAY™ cloning technology (Invitrogen Inc.), which is based on recombination.

The isolated nucleic acid according to the invention can comprise further genetic control sequences or elements, besides the at least one promoter sequence according to the invention.

The concept of the genetic control sequences or elements is to be understood broadly and means all those sequences which have an effect on the origin or the function of the isolated nucleic acid or the transgenic expression cassette according to the invention. Genetic control sequences modify, for example, the transcription and/or translation in prokaryotic or eukaryotic organisms. Preferably, the isolated nucleic acid or the transgenic expression cassettes according to the invention comprise at least one promoter sequence 5'-upstream from the particular nucleic acid sequence to be expressed transgenically and a terminator sequence 3'-downstream as additional genetic control sequence, and, if appropriate, further customary regulatory elements, in each case functionally linked with the nucleic acid sequence to be expressed transgenically.

Genetic control sequences can also comprise further promoters, promoter elements or minimal promoters which are capable of modifying expression-controlling properties. It is thus possible, by means of genetic control sequences, that for example tissue-specific expression takes place in addition in dependence on certain stress factors.

Genetic control sequences furthermore also comprise the 5'-untranslated region, introns, the noncoding 3' region or else sequences of genes. It has been shown that 5'-untranslated sequences are capable of enhancing the transient expression of heterologous genes. Furthermore, they may promote tissue specificity (Rouster J et al. (1998) Plant J 15:435-440). Conversely, the 5'-untranslated region of the opaque-2 gene suppresses expression. Deletion of the region in question results in an increase in gene activity (Lohmer S et al. (1993) Plant Cell 5:65-73).

The isolated nucleic acid can advantageously comprise one or more of what are known as enhancer sequences in functional linkage with the promoter, which make increased transgenic expression of the nucleic acid sequence possible. Additional advantageous sequences can also be inserted at the 3' end of the nucleic acid sequences to be expressed transgenically, such as further regulatory elements or terminators. The nucleic acid sequences to be expressed transgenically can be present as one or more copies in one of the transgenic expression cassettes according to the invention.

Control sequences are furthermore understood as meaning those which make possible homologous recombination or insertion into the genome of a host organism, or which permit deletion from the genome. In the case of homologous recombination, one of the promoters according to the invention may be substituted for the natural promoter of a particular gene, for example. Such sequences are to be understood as genetic control sequences. Methods such as the cre/lox technology permit tissue-specific, and in some circumstances inducible, deletion of the transgenic expression cassette from the genome of the host organism (Sauer B (1998) Methods (Duluth) 14(4):381-92). Here, certain flanking sequences are added to the target gene (lox sequences), which later make possible deletion by means of cre recombinase.

To select cells which have successfully undergone homologous recombination, or else transformation, it is, as a rule, necessary additionally to introduce a selectable marker (see hereinbelow). Homologous recombination is a relatively rare event in higher eukaryotes, in particular in plants. Random integrations into the host genome predominate. One possibility of deleting the randomly integrated sequences, and thus to increase the concentration of cell clones with a correct homologous recombination, is the use of a sequence-specific recombination system as described in U.S. Pat. No. 6,110,736.

Polyadenylation signals which are suitable as control sequences comprise plant polyadenylation signals and preferably those which essentially correspond to T-DNA polyadenylation signals from *Agrobacterium tumefaciens*. In a particularly preferred embodiment, the isolated nucleic acid or the transgenic expression cassette comprises a terminator sequence which is functional in plants. Terminator sequences which are functional in plants generally means those sequences which are capable of bringing about, in plants, the termination of the transcription of a DNA sequence. Examples of suitable terminator sequences are the OCS (octopine synthase) terminator and the NOS (nopalin synthase) terminator. However, plant terminator sequences are especially preferred. Plant terminator sequences generally refers to those sequences which are part of a natural plant gene. Especially preferred in this context is the terminator of the potato cathepsin D inhibitor gene or the terminator of the field bean storage protein gene VfLE1B3. These terminators are at least equivalent to the viral or T-DNA terminators described in the prior art.

The isolated nucleic acid or the transgenic expression cassettes according to the invention and vectors comprising those may comprise further functional elements. The term functional element is to be understood broadly and means all those elements which have an effect on the generation, multiplication or function of the transgenic expression cassettes according to the invention or on transgenic expression vectors or organisms derived from them. The following may be mentioned by way of example, but not by limitation:

1. Selection Markers

The term "selection marker" comprises not only positive selection markers, which confer a resistance to an antibiotic, herbicide or other biocide, but also negative selection markers, which confer a sensitivity to precisely the abovementioned, and also markers which confer a growth advantage to the transformed organism (for example by expression of key genes of cytokinin biosynthesis; Ebinuma H et al. (2000) Proc Natl Acad Sci USA 94:2117-2121). In the case of positive selection, only those organisms which express the selection marker in question thrive, while precisely these organisms die in the case of negative selection. The use of a positive selection marker is preferred in the generation of transgenic plants. Furthermore preferred is the use of selection markers which confer growth advantages. Negative selection markers can be used advantageously when the task at hand consists in eliminating certain genes or genome segments from an organism (for example for the purposes of a hybridization process).

i) Positive Selection Markers: The selectable marker introduced with the transgenic expression cassette confers resistance to a biocide, for example a herbicide (such as phosphinothricin, glyphosate or bromoxynil), a metabolic inhibitor (such as 2-deoxyglucose-6-phosphate; WO 98/45456) or an antibiotic (such as, for example, tetracyclins, ampicillin, kanamycin, G 418, neomycin, bleomycin or hygromycin) to the successfully transformed cells. The selection marker permits the selection of the transformed cells from untransformed cells (McCormick et al. (1986) Plant Cell Reports 5:81-84). Especially preferred selection markers are those which confer resistance to herbicides.

ii) Negative Selection Markers: Negative selection markers make possible for example the selection of organisms with successfully deleted sequences which comprise the marker gene (Koprek T et al. (1999) The Plant Journal 19(6):719-726). When carrying out a negative selection, for example a compound which otherwise has no disadvantageous effect on the plant is converted into a compound which is disadvantageous, for example owing to the negative selection marker introduced into the plant. Genes which have a disadvantageous effect per se are furthermore suitable.

2) Reporter Genes

Reporter genes encode readily quantifiable proteins which, via their colour or enzyme activity, allow an assessment of the transformation efficiency, the site or time of expression (see also Schenbron E, Groskreutz D. Mol Biotechnol. 1999; 13(1):29-44). Examples which may be mentioned are: "green fluorescence protein" (GFP) (Chui W L et al. (1996), Curr Biol 6:325-330; Leffel S M et al. (1997) Biotechniques 23(5): 912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228). Chloramphenicol transferase (Fromm et al. (1985) Proc Natl Acad Sci USA 82:5824-5828), Luciferase (Millar et al. (1992) Plant Mol Biol Rep 10:324-414; Ow et al. (1986) Science 234:856-859); allows detection via bioluminescence. β-Galactosidase, encodes an enzyme for which a variety of chromogenic substrates are available. β-Glucuronidase (GUS) (Jefferson et al. (1987) EMBO J. 6:3901-3907) or the uidA gene, which encodes an enzyme for a variety of chromogenic substrates. R-Locus gene product: protein which regulates the production of anthocyanine pigments (red coloration) in plant tissue and thus makes possible the direct analysis of the promoter activity without addition of further auxiliary substances or chromogenic substrates (Dellaporta et al. (1988) In: Chromosome Structure and Function: Impact of New Concepts, 18th Stadler Genetics Symposium, 11:263-282). Tyrosinase (Katz et al. (1983) J Gen Microbiol 129: 2703-2714), an enzyme which oxidizes tyrosine to DOPA and dopaquinone, which subsequently form melanin, which can be detected readily. Aequorin (Prasher et al. (1985) Biochem Biophys Res Commun 126(3):1259-1268), can be used in the calcium-sensitive bioluminescence detection.

3) Replication Origins

Replication origins ensure the multiplication of the transgenic expression cassettes or transgenic expression vectors according to the invention in, for example, *E. coli* or agrobacteria. Examples which may be mentioned are OR1 (origin of DNA replication), the pBR322 on or the P15A on (Sambrook et al.: Molecular Cloning. A Laboratory Manual, 2<nd> ed. Cold Spring Harbor Laboratory Press, Cold Spring Harbor, N.Y., 1989). Examples of replication origins which are functional in *Agrobacterium* are pRK2, pRi, PVS1 or pSA.

4) Border Sequences

"Border sequences" (such as, for example, the right or left border of the T-DNA) allow an agrobacteria-mediated transfer into plant cells for the transfer and integration into the plant genome.

5) Multiple Cloning Sites (MCS) Permit and Facilitate the Insertion of One or More Nucleic Acid Sequences.

The invention also relates to vectors which comprise the above-described isolated nucleic acid of the invention or the transgenic expression cassette of the invention. Vectors generally means structures which are capable of replication and which are preferably host-specific, and which allow the uptake of nucleic acid sequences and their transfer into other cells. Examples of vectors can be plasmids, cosmids, phages, viruses or else agrobacteria. Vectors which are particularly suitable for the purposes of plant biotechnology are described exemplarily hereinbelow. Vectors of the present invention comprise transgenic expression vectors.

Another subject of the invention relates to transgenic organisms transiently or stably transformed or transfected with at least one isolated nucleic acid of the invention or at least one transgenic expression cassette according to the invention or at least one vector according to the invention or to progeny of such transgenic organisms. Furthermore the present invention relates to cells, cell cultures, tissues, parts- such as, for example in the case of plant organisms, leaves, roots and the like—or propagation material derived from such organisms, e.g. to seeds of transgenic organisms of the invention. It is understood that for the purpose of the present invention the term transgenic organism not only encompasses the organism where the nucleic acid of the invention has been transiently or stably introduced, but also refers to the progeny of such organisms irrespective of the generation distance, e.g. progeny of first generation as well as progeny of the $X^{th}$ generation, provided that these organisms still comprise the nucleic acid of the invention.

Preferably the transgenic organism is a plant or a microorganism, more preferably the transgenic organism is a plant selected from the family Brassicaceae, even more preferably from the genera *Brassica* or *Arabidopsis*.

Organisms, starting organisms or host organisms are understood as meaning prokaryotic or eukaryotic organisms such as, for example, microorganisms or plant organisms. Preferred microorganisms are bacteria, yeasts, algae or fungi.

Preferred bacteria are bacteria of the genus *Escherichia, Erwinia, Agrobacterium, Flavobacterium, Alcaligenes* or *cyanobacteria*, for example of the genus *Synechocystis*.

Especially preferred are microorganisms which are capable of infecting plants and thus of transferring the nucleic acid, the transgenic expression cassette and/or the vector of the invention. Preferred microorganisms are those from the genus *Agrobacterium* and in particular the species *Agrobacterium tumefaciens*.

Host or starting organisms which are preferred as transgenic organisms are, above all, plant organisms. Plant organisms generally means all those organisms which are capable of photosynthesis. Included as plant organisms within the scope of the invention are all genera and species of the higher and lower plants of the plant kingdom. The mature plants, seeds, tubers, beets/swollen tap roots, fruits, shoots and seedlings and also parts, propagation material and cultures, for example cell cultures, derived therefrom are also included. Mature plants means plants at any developmental stage beyond the seedling. Seedling means a young immature plant in an early developmental stage. Annual, perennial, monocotyledonous and dicotyledonous plants are preferred host organisms for preparing transgenic plants. Preference is given to plants of the following plant family: Brassicaceae in particular to plants of the genera *Brassica* and *Arabidopsis*.

The preparation of a transformed organism or of a transformed cell requires introducing the appropriate DNA into the appropriate host cell. A multiplicity of methods is available for this process which is referred to as transformation (see also Keown et al. 1990 Methods in Enzymology 185: 527-537). Thus, by way of example, the DNA may be introduced directly by microinjection or by bombardment with DNA-coated microparticles. The cell may also be permeabilized chemically, for example using polyethylene glycol, so that the DNA can enter the cell via diffusion. The DNA may also be performed via protoplast fusion with other DNA-containing units such as minicells, cells, lysosomes or liposomes. Another suitable method for introducing DNA is electroporation in which the cells are reversibly permeabilized by an electric impulse.

In the case of plants, the methods described for transforming and regenerating plants from plant tissues or plant cells are utilized for transient or stable transformation. Suitable methods are especially protoplast transformation by polyethylene glycol-induced DNA uptake, the biolistic method using the gene gun, the "particle bombardment" method, electroporation, the incubation of dry embryos in DNA-containing solution and microinjection.

Apart from these "direct" transformation techniques, a transformation may also be carried out by bacterial infection by means of Agrobacterium tumefaciens or Agrobacterium rhizogenes. These strains contain a plasmid (Ti or Ri plasmid), a part of which (what is known as T-DNA) is transferred to the plant after infection with Agrobacterium and integrated into the genome of the plant cell. The Agrobacterium-mediated transformation is best suited to dicotyledonous plant cells, whereas the direct transformation techniques are suitable for any cell type.

A transgenic expression cassette of the invention may be introduced advantageously into cells, preferably into plant cells, by using vectors, preferably vectors of the invention.

In an advantageous embodiment, the transgenic expression cassette is introduced by means of plasmid vectors. Preference is given to those transgenic expression vectors which enable a stable integration of the transgenic expression cassette into the host genome. In this context, host genome means the entire hereditary information of the host and comprises for example not only the chromosomal DNA of the nucleus, but also the DNA of the plastids and mitochondria. However, the insertion into the chromosomal DNA of the nucleus is preferred.

In the case of injection or electroporation of DNA into plant cells, no particular demands on the plasmid used are made. It is possible to use simple plasmids such as those of the pUC series. If complete plants are to be regenerated from the transformed cells, it is necessary for an additional selectable marker gene to be present on the plasmid.

Transformation techniques have been described for various monocotyledonous and dicotyledonous plant organisms. Furthermore, various possible plasmid vectors which normally contain a replication origin for propagation in E. coli and a marker gene for selection of transformed bacteria are available for introducing foreign genes into plants. Examples are pBR322, pUC series, M13 mp series, pACYC184 etc.

The transgenic expression cassette may be introduced into the vector via a suitable restriction cleavage site. The resultant plasmid is first introduced into E. coli. Correctly transformed E. coli cells are selected, cultivated and the recombinant plasmid is obtained using methods familiar to the skilled worker. Restriction analysis and sequencing may be used in order to check the cloning step.

Transformed cells, i.e. those which contain the introduced DNA integrated into the DNA of the host cell may be selected from untransformed cells, if a selectable marker is part of the introduced DNA. A marker may be, by way of example, any gene which is capable of imparting a resistance to antibiotics or herbicides. Transformed cells which express such a marker gene are capable of surviving in the presence of concentrations of an appropriate antibiotic or herbicide, which kill an untransformed wild type. Examples are the bar gene which imparts resistance to the herbicide phosphinothricin (Rathore K S et al., Plant Mol Biol. 1993 March; 21(5):871-884), the nptll gene which imparts resistance to kanamycin, the hpt gene which imparts resistance to hygromycin and the EPSP gene which imparts resistance to the herbicide glyphosate.

Depending on the method of DNA introduction, further genes may be required on the vector plasmid. If agrobacteria are used, the transgenic expression cassette is to be integrated into specific plasmids, either into an intermediate vector (shuttle vector) or a binary vector. If, for example, a Ti or Ri plasmid is to be used for transformation, at least the right border, in most cases, however, the right and the left border, of the Ti or Ri plasmid T-DNA is connected as flanking region with the transgenic expression cassette to be introduced. Preference is given to using binary vectors. Binary vectors can replicate both in E. coli and in Agrobacterium. They normally contain a selection marker gene and a linker or polylinker flanked by the right and left T-DNA border sequences. They may be transformed directly into Agrobacterium (Holsters et al., Mol. Gen. Genet. 163 (1978), 181-187). The selection marker gene permits selection of transformed agrobacteria; an example is the nptll gene which imparts a resistance to kanamycin. The Agrobacterium which in this case acts as the host organism should already contain a plasmid with the vir region. This region is required for the transfer of T-DNA onto the plant cell. An Agrobacterium transformed in this way may be used for transformation of plant cells.

The use of T-DNA for transformation of plant cells has been intensely studied and described (B. Jenes et al., Techniques for Gene Transfer, in: Transgenic Plants, Vol. 1, Engineering and Utilization, edited by Kung S D and Wu R, Academic Press (1993), pp. 128-143 and in Potrykus (1991) Annu Rev Plant Physiol Plant Molec Biol 42:205-225; EP 120516; Hoekema, In: The Binary Plant Vector System, Offsetdrukkerij Kanters B. V., Alblasserdam, Chapter V; Fraley et al., Crit. Rev. Plant. Sci., 4:1-46 and An et al. (1985) EMBO J. 4:277-287). Various binary vectors are known and partly commercially available, such as, for example, pBIN19 (Bevan et al. (1984) Nucl Acids Res 12:8711f.; Clontech Laboratories, Inc. USA) or PSUN derivatives (SunGene GmbH & Co. KGaA; WO 02/00900). The expression cassette according to the invention can be inserted into these binary vectors and integrated into the plant genome as described hereinabove and/or hereinbelow.

The DNA is transferred into the plant cell by coculturing plant explants with Agrobacterium tumefaciens or Agrobacterium rhizogenes. Starting from infected plant material (e.g. leaf, root or stem parts, but also protoplasts or plant cell suspensions), it is possible to regenerate whole plants by using a suitable medium which may contain, for example, antibiotics or biocides for selection of transformed cells. The plants obtained may then be screened for the presence of the introduced DNA, in this case the transgenic expression cassette of the invention. As soon as the DNA has integrated into the host genome, the corresponding genotype is normally stable and the corresponding insertion is also found again in subsequent generations. Normally, the integrated transgenic expression cassette contains a selection marker which imparts to the transformed plant a resistance to a biocide (for example a herbicide), a metabolism inhibitor such as 2-DOG or an antibiotic such as kanamycin, G 418, bleomycin, hygromycin or phosphinothricin etc. The selection marker allows the selection of transformed cells from untransformed cells (McCormick et al. (1986) Plant Cell Reports 5:81-84). The plants obtained may be cultivated and crossed in the common manner. Two or more generations should be cultured in order to ensure that the genomic integration is stable and heritable.

As soon as a transformed plant cell has been prepared, it is possible to obtain a complete plant by using methods known to the skilled worker. To this end, callus cultures are used as starting point, by way of example. From these still undifferentiated cell masses, it is possible to induce formation of shoot and root in the known manner. The shoots obtained can be planted out and cultivated.

The integration of the T-DNA can be determined e.g. on the basis of the efficacy of expression of the nucleic acids to be expressed transgenically or of the selection marker for example in vitro by shoot meristem propagation using one of the above-described selection methods.

The invention further relates to cells, cell cultures, parts, such as, for example, roots, leaves, etc. in the case of transgenic plant organisms, and transgenic propagation material such as seeds, tubers, beets/swollen tap roots or fruits derived from the above-described transgenic organisms and/or comprising an isolated nucleic acid of the invention, a transgenic expression cassette of the invention or a vector of the invention.

Genetically modified plants of the invention, which can be consumed by humans and animals, may also be used, for example directly or after preparation known per se, as foodstuffs or feedstuffs.

The invention further relates to the use of the above-described transgenic organisms of the invention and of the cells, cell cultures, parts, such as, for example, roots, leaves, etc., in the case of transgenic plant organisms, and transgenic propagation material such as seeds, tubers, beets/swollen tap roots or fruits derived from them for the production of food- or feedstuffs, pharmaceuticals or fine chemicals.

The invention also relates to the use of an isolated nucleic acid of the invention, an expression cassette according to the invention or a vector of the invention for the manufacturing of a transgenic plant.

The present invention further relates to a method for the manufacturing of a transgenic plant, comprising the steps:

a) introducing into one or more plant cells an isolated nucleic acid of the invention, an expression cassette of the invention or a vector of the invention in order to produce transgenic cells; and b) selection of transgenic cells which comprise said isolated nucleic acid, expression cassette or vector of the invention stably integrated into the genome; and c) regeneration of intact plants from said transgenic cells.

Information on how these steps may be performed is given in detail hereinabove.

Furthermore, the present invention relates to a method for improving plant shoot growth, comprising:

i) introducing into a plant an isolated nucleic acid of the invention; and ii) expressing the introduced nucleic acid of the invention.

In the following the present invention is further described by way of examples.

BRIEF DESCRIPTION OF THE DRAWINGS

Figures

DETAILED DESCRIPTION OF THE PRESENTLY PREFERRED EMBODIMENTS

Examples

Material and Methods

Figure 1:
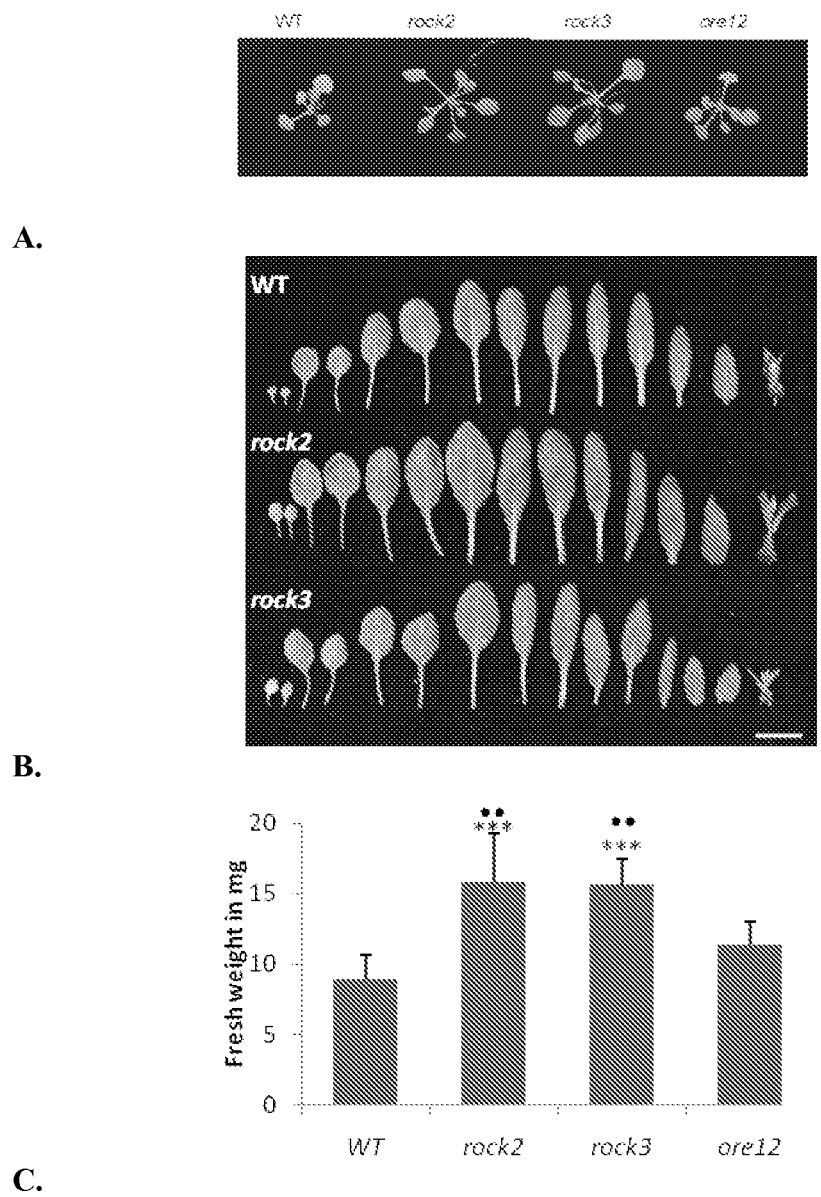
FIG. 1 shows vegetative growth of rock2, rock3 and ore12 mutants in comparison to wild type: (A.) Photo of seedlings 19 DAG (days after germination). Plants were grown under long-day conditions. (B.) Comparison of leaves from plants shown in (A.), without ore12. (C.) Comparison of fresh weight 18 DAG. n=10; *,•=p<0.01; , ••=p<0,005; *, •••=p<0.0001. *=compared to WT; •=compared to ore12.

The rock2 and rock3 alleles were identified and isolated based on their ability to suppress the phenotypic consequences of cytokinin deficiency caused by the overexpression of a CKX gene encoding a cytokinin oxidase/dehydrogenase.

Plant Material and Growth Conditions

The Columbia (Col-0) ecotype of *Arabidopsis thaliana* was used as the wild type. Plants were grown in the greenhouse on soil or under sterile conditions in Petri dishes containing ATS-medium (Estelle, M. A., and Somerville, C. (1986). Auxin-resistant mutants of *Arabidopsis thaliana* with an altered morphology. Mol. Gen. Genet. 206, 200-206). All plants were grown at 22° C. under long-day conditions (16 h light/8 h dark).

Mutagenesis

Approximately 25000 35S:CKX1 seeds (Werner, T., Motyka, V., Laucou, V., Smets, R., Van Onckelen, H., and Schmülling, T. (2003). Cytokinin-deficient transgenic *Arabidopsis* plants show multiple developmental alterations indicating opposite functions of cytokinins in the regulation of shoot and root meristem activity. Plant Cell 15, 2532-2550) were soaked for 16 h in 100 ml 0.2% (v/v) ethyl methane sulfonate at room temperature. The M1 generation was grown as single plants and the M2 generation was screened for plants with wild-type-like phenotype.

Genetic Analysis

Mapping populations for rock2 and rock3 were generated by crossing the rock2 35S:CKX1 and rock3 35S:CKX1 plants with wild type ecotype Landsberg erecta. The F2 progeny plants were used to map rock2 and rock3.

In order to analyze the consequences of the rock2 and rock3 mutations in wild type, the rock2 and rock3 suppressor mutants in 35S:CKX1 background were crossed to wild-type Columbia. F1 progeny plants from this cross were still showing the revertant phenotype suggesting that the rock2 and rock3 allels are dominant. The F2 generation was screened for rock2 and rock3 plants in wild-type background (called then rock2 and rock3 mutants).

Establishment of Transgenic Lines

For the construction of the pAHK2:rock2 transgene a 2124 by promoter region of AHK2 was amplified by PCR from genomic DNA of *A. thaliana* Col-0 and cloned with Gateway™ technology into the pDONR™ P4-P1R entry vector (Invitrogen, Karlsruhe, Germany). After cloning the AHK2 coding sequence with Gateway™ technology into the pDONR™ 221 entry vector (Invitrogen) the rock2 point mutation was introduced by PCR based mutagenesis with the "QuickChange Site-Directed Mutagenesis"-Kit (Stratagene, La Jolla, USA) to obtain the rock2 Allele. Both fragments were combined with Multisite Gateway™ recombinational cloning in the pK7m24GW,3 vector (Karimi et al., 2005). To obtain the pAHK3:rock3 construct a 2062 bp promoter region of AHK3 was amplified by PCR from genomic DNA of *A. thaliana* Col-0 and the fragment was inserted into pDONR™P4-P1R entry vector (Invitrogen). The AHK3 cDNA containing the open reading frame of the gene was PCR-amplified from *A. thaliana* Col-0 and cloned into pDONR™222 entry vector (Invitrogen). To introduce the rock3 point mutation the "QuickChange Site-Directed Mutagenesis"-Kit (Stratagene, La Jolla, USA) was used to get the rock3 allele. The AHK3 promoter and the ROCK3 cDNA were combined with Multisite Gateway™ recombinational cloning in the pK7m24GW,3 vector (Karimi, M., De Meyer, B., and Nilson, P. (2005). Modular cloning in plant cells. Trends Plant Sci. 10, 103-105). Both constructs were introduced into *Agrobacterium tumefaciens* strain GV3101 and *A. thaliana* Col-0 plants were transformed using the floral-dip method (Clough, S. J., and Bent, A. F. (1998). Floral dip: a simplified method for *Agrobacterium*-mediated transformation of *Arabidopsis thaliana*. Plant J. 16, 735-743). Transgenic lines were selected using kanamycin and propagated into the T3 or T4 generation.

Morphometric Measurements

At 18 days after germination digital pictures were taken of rosettes and the rosette diameter was measured using the Scion Image program (Scion Corporation, Frederick, Md., USA). Flowers at stage 14 were photographed and their size was also measured using the Scion Image program.

Determination of Fresh Weight, Final Plant Height and Yield Parameters

Fresh weights were measured by weighting either rosettes, shoots without rosettes, or whole aerial parts of the plants. The final plant height and the number of siliques were determined after termination of flowering. For analysis of seed yield, plants were put into paper bags after termination of flowering. After plants were kept dry for additional three weeks, total seed weight was determined.

Photosynthetic Parameters

The maximum efficiency of PSII photochemistry (Fv/Fm ratio) of dark adapted plants was measured with FluorCam (Photon Systems Instruments, Brno, Czech Republic). Chlorophyll contents of individual leaves were measured using the Chlorophyll Meter SPAD-502 (Konika Minolta, Bremen, Germany), taking the mean value of two measurements on the same leaf.

Results

1. Analysis of Mutant Alleles in the 35S:CKX1 Background

In order to compare the consequences of the rock3 mutation with those of the ore12 mutation the latter was introgressed into the 35S:CKX1 background (the rock3 was identified in this background). It could be shown that the ore12 mutation reverts partially the phenotypic consequences of CKX1 overexpression. However, at different time points during development the degree of reversion is less strong than the reversion achieved with the rock3 allele. This difference is most evident for seedling size and rosette diameter. These two parameters are good indicators for a changed cytokinin status of the CKX1ox plants.

2. Analysis of Mutant Alleles in Wild Type Background

Next the consequences of all three mutant alleles (rock2, rock3 and ore12) in the wild-type background (Col-0) were compared. In FIG. 1 it is shown that only rock2 and rock3 allels significantly enhance the vegetative growth of wild-type plants, whereas the ore12 allel does not result in significant growth enhancement. This effect can already be seen early after seed germination (FIG. 1A) and is also evident from leaf size comparison at a later developmental stage (FIG. 1B). The effects of the rock2 and rock3 alleles were not only significantly stronger compared to wild type plants but also compared to the ore12 allel. Both rock2 and rock3 caused a >75% increase of fresh weight at 18 days after germination (DAG) compared to wild type. An analysis of the increase of fresh weight of rosettes and the whole plant over the complete life cycle of plants showed that the increase in fresh weight difference is particularly evident at 32-40 DAG and that the effect is strongest with the rock2 allele.

Figure 2:
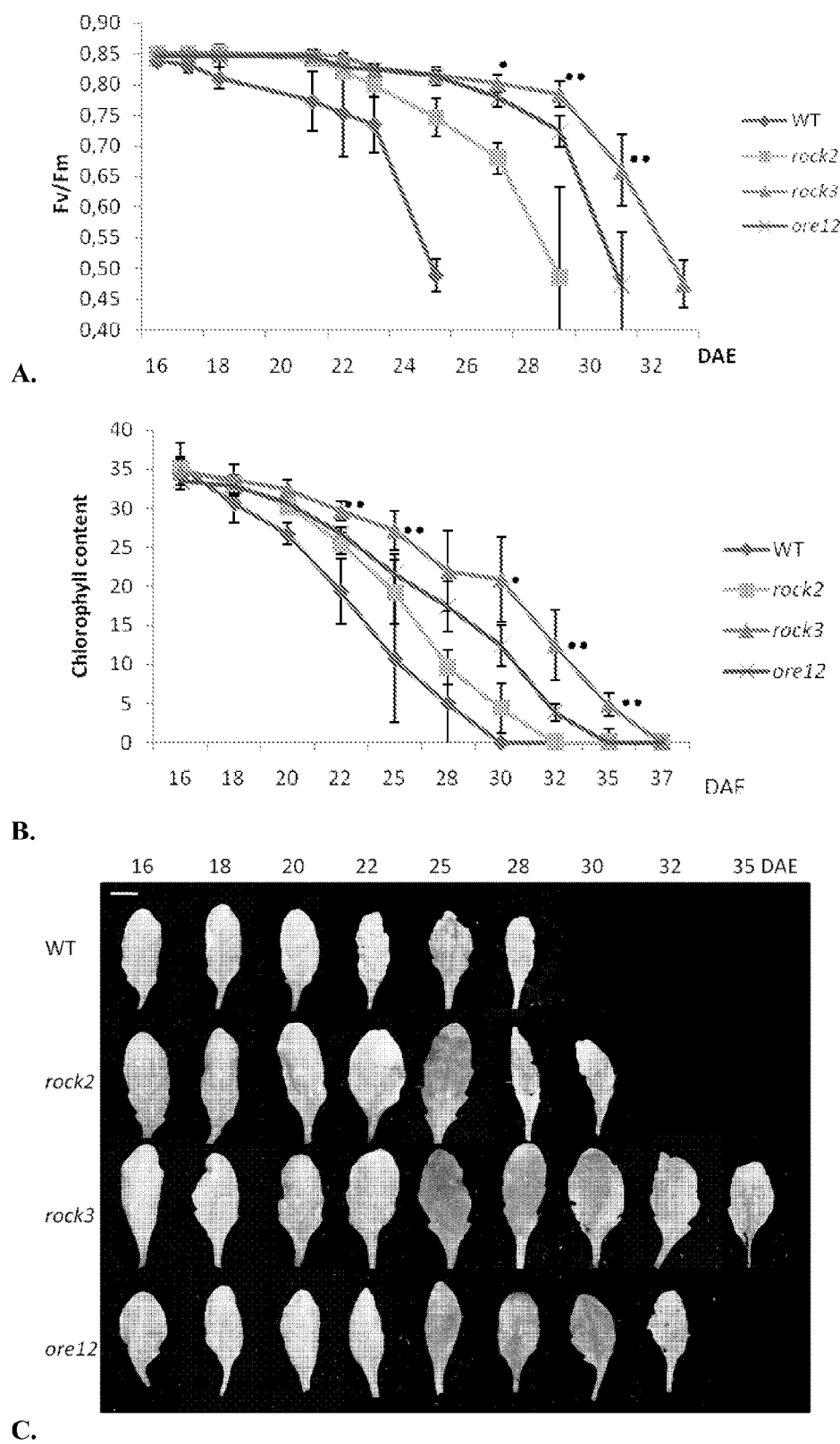
FIG. 2 shows natural senescence of leaf 6 of rock and ore12 mutant plants under long day conditions: (A.) Reduction of photosynthetic efficiency of photosystem II from 16 to 37 DAE (days after emergence). (B.) Reduction of the chlorophyll content 16 to 35 DAE. (C.) Comparison of leaves from plants shown in (A.) and (B.). n=10; •=p<0.01; ••=p<0.005 compared to ore12.

It is known that the enhanced cytokinin status caused by the ore12 allele delays leaf senescence. Leaf senescence in wild-type plants, ore12 mutant plants and the rock mutants was compared. FIG. 2 shows clearly a retarded onset of leaf senescence in all mutant plants compared to wild type. Photosynthetic efficiency of PS II (Fv/Fm) started to decline in the 6's rosette leaf of wild-type plants around 17 DAE and around 21 to 23 DAE in the mutant plants (FIG. 2A). Among these, rock2 plants showed the earliest onset of leaf senescence, followed by ore12 and rock3. This difference in timing of leaf senescence was maintained leading to an about ten days longer life time of rock3 leaves compared to wild-type leaves (FIG. 2A). This result was confirmed by measuring another parameter of senescence, the decrease of chlorophyll (FIG. 2B), as well as visual inspection of the leaves (FIG. 2C).

3. Analysis of Transgenic Expression of Rock Alleles

Figure 3:
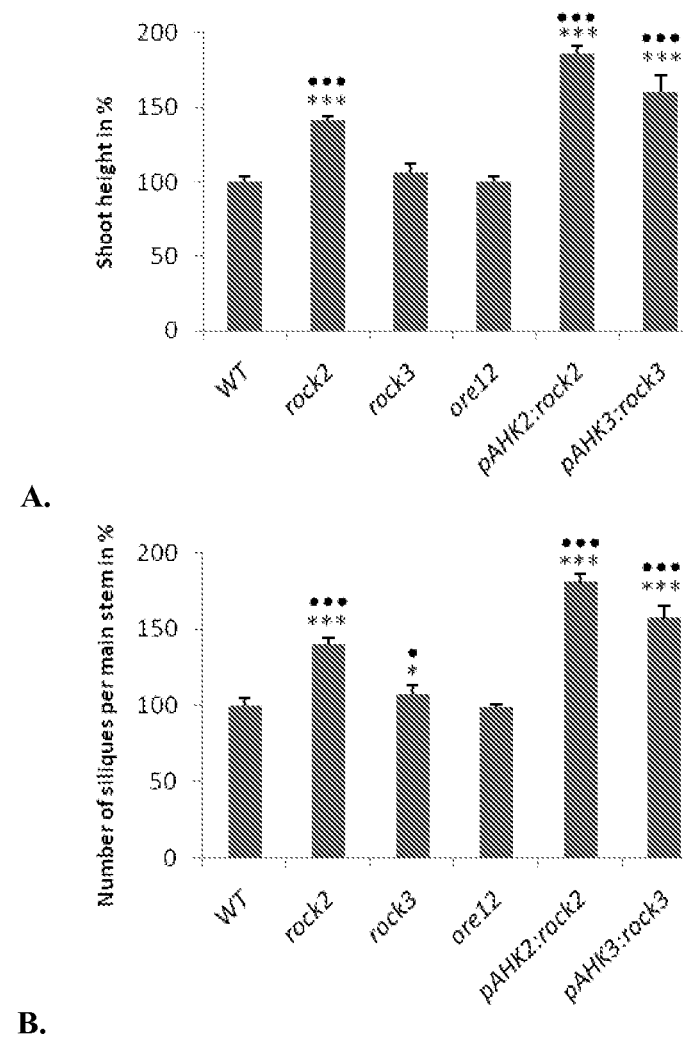
FIG. 3 shows shoot parameter of rock2, rock3 and ore12 mutant plants and transgenic lines expressing pAHK2:rock2 or pAHK3:rock3. (A.) The plant height of rock2 and transgenic rock2 and rock3 mutant plants is increased. (B.) rock2 mutants and transgenic rock2 and rock3 lines form more siliques on the main stem. n=10; *, •=p<0.01; ***, •••=p<0.0001; *=compared to WT; •=compared to ore12.
Figure 4:
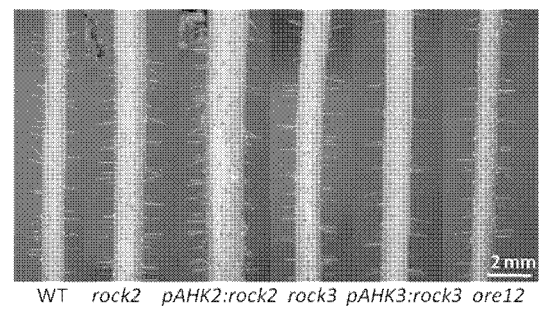
FIG. 4 shows shoot parameter of rock2, rock3 and ore12 mutant plants and transgenic lines expressing pAHK2:rock2 or pAHK3:rock3: (A., B.) rock2 and rock3 mutants and transgenic rock2 and rock3 lines form (A.) thicker stems and (B.) bigger flowers. n=10; ***, •••=p<0.0001; *=compared to WT; •=compared to ore12.
Figure 4:
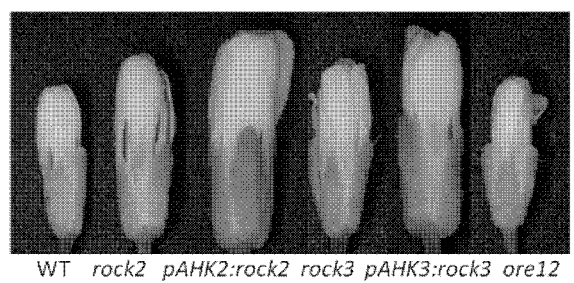
Figure 4:
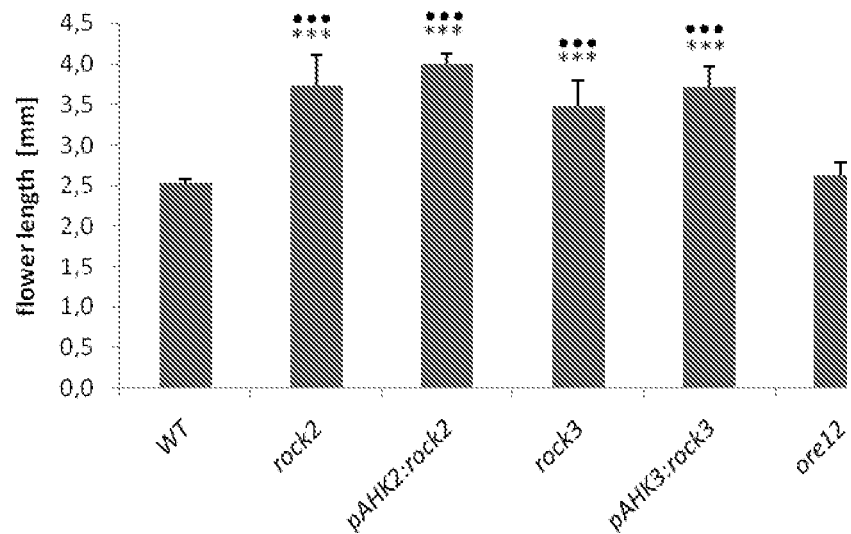
Figure 5:
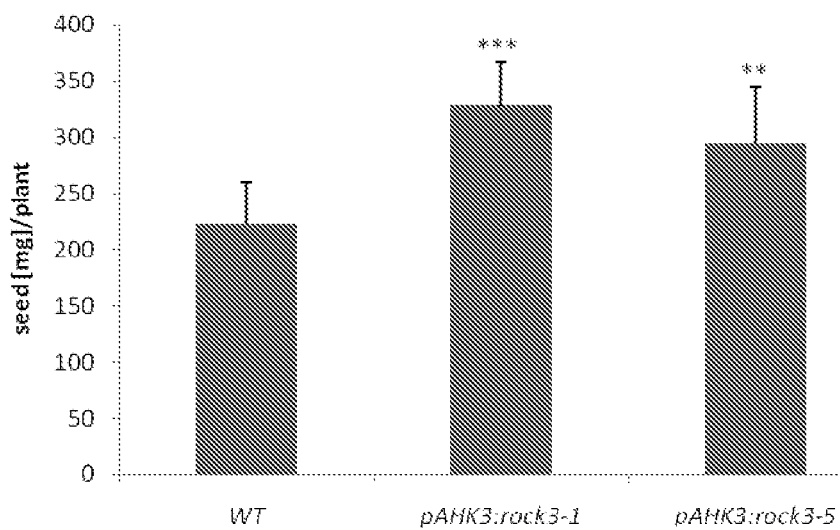
FIG. 5 shows seed yield of two independent pAHK3:rock3 transgenic lines compared to wild type. Transgenic lines have an up to 47% increase of seed yield compared to wild-type plants. n=10. =p<0.005; *=p<0.0001 compared to WT.

In the next step the consequences of transgenic expression of the dominant rock alleles were analysed. To this end we transformed *Arabidopsis* Col-0 plants with genes comprising ca. 2 kb of the 5' upstream regulatory regions of AHK2 and AHK3 respectively and the rock2 and rock3 coding sequences, respectively. These genes were named pAHK2:rock2 and pAHK3:rock3, respectively, and are labelled pAHK2:rock2 and pAHK3:rock3 in FIG. 3 to FIG. 5. Generally it was found a further enhancement of the phenotypic traits that were altered in the rock mutant plants. FIGS. 3 and 4 show that pAHK2:rock2 and pAHK3:rock3 transgenic plants have compared to wild-type or ore12 plants a significant increase in shoot height (FIG. 3A), a significantly increased number of siliques on the main stem (FIG. 3B), thicker stems caused by an enhanced number of larger cells in the radial dimension (FIG. 4A) and a significantly increased size of flowers (FIG. 4B). As demonstrated in FIG. 5, it could be shown that pAHK3:rock3 transgenic plants have a significantly higher seed yield compared to wild type.

The invention claimed is:

1. An isolated nucleic acid, comprising a nucleic acid sequence encoding a constitutively active variant of the cytokinin receptor *Arabidopsis* histidine kinase 2 (AHK2) comprising the amino acid sequence of SEQ ID NO: 1.

2. An isolated nucleic acid, comprising a nucleic acid sequence encoding a constitutively active variant of the cytokinin receptor *Arabidopsis* histidine kinase 3 (AHK3) comprising the amino acid sequence of SEQ ID NO: 2.

3. The isolated nucleic acid of claim 2, further comprising at least one promoter sequence, wherein the at least one promoter sequence and the coding nucleic acid sequence are functionally linked with one another.

4. A vector comprising the isolated nucleic acid of claim 1.

5. A vector comprising the isolated nucleic acid of claim 2.

6. A transgenic organism transiently or stably transformed or transfected with the isolated nucleic acid of claim 1, wherein the organism is a plant of the plant family Brassicaceae.

7. A transgenic organism transiently or stably transformed or transfected with the isolated nucleic acid of claim 2, wherein the organism is a plant of the plant family Brassicaceae.

8. A cell comprising the isolated nucleic acid of claim 1.

9. A cell comprising the isolated nucleic acid of claim 2.

10. A cell comprising the vector of claim 4.

11. A method for the manufacturing of a transgenic plant of the plant family Brassicaceae, comprising the following steps:
   a) introducing into one or more plant cells the isolated nucleic acid of claim 1 to produce transgenic cells;
   b) selecting transgenic cells which comprise said isolated nucleic acid; and
   c) regenerating intact plants from said transgenic cells.

12. A method for the manufacturing of a transgenic plant of the plant family Brassicaceae, comprising the following steps:
   a) introducing into one or more plant cells the isolated nucleic acid of claim 2 in order to produce transgenic cells;
   b) selecting transgenic cells which comprise said isolated nucleic acid; and
   c) regenerating intact plants from said transgenic cells.

13. A method for the manufacturing of a transgenic plant of the plant family Brassicaceae, comprising the following steps:
   a) introducing into one or more plant cells the vector of claim 4 in order to produce transgenic cells;
   b) selecting transgenic cells which comprise said isolated nucleic acid or vector stably integrated into the genome; and
   c) regenerating intact plants from said transgenic cells.

14. The isolated polypeptide encoded by the isolated nucleic acid of claim 1.

15. A method for improving shoot growth in a plant of the plant family Brassicaceae compared to a control plant of the plant family Brassicaceae, comprising:
   (a) introducing into the plant the isolated nucleic acid of claim 1; and
   (b) expressing the introduced nucleic acid of claim 1.

16. A method for improving shoot growth in a plant of the plant family Brassicaceae compared to a control plant of the plant family Brassicaceae, comprising:
   (a) introducing into the plant the isolated nucleic acid of claim 2; and
   (b) expressing the introduced nucleic acid of claim 2.

17. The isolated nucleic acid of claim 1, further comprising at least one promoter sequence, wherein the at least one promoter sequence and the coding nucleic acid sequence are functionally linked with one another.

18. An isolated polypeptide encoded by the isolated nucleic acid of claim 2.

19. The transgenic organism of claim 6, wherein the plant is *Arabidopsis thaliana*.

20. The transgenic organism of claim 7, wherein the plant is *Arabidopsis thaliana*.

21. The method for the manufacturing of the transgenic plant of claim 11, wherein the plant is *Arabidopsis thaliana*.

22. The method for the manufacturing of the transgenic plant of claim 12, wherein the plant is *Arabidopsis thaliana*.

23. The method for the manufacturing of the transgenic plant of claim 13, wherein the plant is *Arabidopsis thaliana*.

24. The method for improving shoot growth in the plant of claim 15, wherein the plant is *Arabidopsis thaliana*.

25. The method for improving shoot growth in the plant of claim 16, wherein the plant is *Arabidopsis thaliana*.

26. An expression cassette comprising the isolated nucleic acid of claim 1.

27. A method for the manufacturing of a transgenic plant of the plant family Brassicaceae, comprising the following steps:
   a) introducing into one or more plant cells the expression cassette of claim 26 to produce transgenic cells;
   b) selecting transgenic cells which comprise said expression cassette; and
   c) regenerating intact plants from said transgenic cells.

28. An expression cassette comprising the isolated nucleic acid of claim 2.

29. A method for the manufacturing of a transgenic plant of the plant family Brassicaceae, comprising the following steps:
   a) introducing into one or more plant cells the expression cassette of claim 27 to produce transgenic cells;
   b) selecting transgenic cells which comprise said expression cassette; and
   c) regenerating intact plants from said transgenic cells.

* * * * *

SEQUENCE LISTING

<160> NUMBER OF SEQ ID NOS: 6

<210> SEQ ID NO 1
<211> LENGTH: 1176
<212> TYPE: PRT
<213> ORGANISM: Arabidopsis thaliana

<400> SEQUENCE: 1

```
Met Ser Ile Thr Cys Glu Leu Leu Asn Leu Thr Ser Lys Lys Ala Lys
1               5                   10                  15

Lys Ser Ser Ser Ser Asp Lys Lys Trp Leu Lys Lys Pro Leu Phe Phe
                20                  25                  30

Leu Ile Leu Cys Gly Ser Leu Val Ile Val Leu Val Met Phe Leu Arg
            35                  40                  45

Leu Gly Arg Ser Gln Lys Glu Glu Thr Asp Ser Cys Asn Gly Glu Glu
        50                  55                  60

Lys Val Leu Tyr Arg His Gln Asn Val Thr Arg Ser Glu Ile His Asp
65                  70                  75                  80

Leu Val Ser Leu Phe Ser Asp Ser Asp Gln Val Thr Ser Phe Glu Cys
                85                  90                  95

His Lys Glu Ser Ser Pro Gly Met Trp Thr Asn Tyr Gly Ile Thr Cys
            100                 105                 110

Ser Leu Ser Val Arg Ser Asp Lys Gln Glu Thr Arg Gly Leu Pro Trp
        115                 120                 125

Asn Leu Gly Leu Gly His Ser Ile Ser Ser Thr Ser Cys Met Cys Gly
130                 135                 140

Asn Leu Glu Pro Ile Leu Gln Gln Pro Glu Asn Leu Glu Glu Glu Asn
145                 150                 155                 160

His Glu Glu Gly Leu Glu Gln Gly Leu Ser Ser Tyr Leu Arg Asn Ala
                165                 170                 175

Trp Trp Cys Leu Ile Leu Gly Val Leu Val Cys His Lys Ile Tyr Val
            180                 185                 190

Ser His Ser Lys Ala Arg Gly Glu Arg Lys Glu Lys Val His Leu Gln
        195                 200                 205

Glu Ala Leu Ala Pro Lys Lys Gln Gln Gln Arg Ala Gln Thr Ser Ser
    210                 215                 220

Arg Gly Ala Gly Arg Trp Arg Lys Asn Ile Leu Leu Gly Ile Leu
225                 230                 235                 240

Gly Gly Val Ser Phe Ser Val Trp Trp Phe Trp Asp Thr Asn Glu Glu
                245                 250                 255

Ile Ile Met Lys Arg Arg Glu Thr Leu Ala Asn Met Cys Asp Glu Arg
            260                 265                 270

Ala Arg Val Leu Gln Asp Gln Phe Asn Val Ser Leu Asn His Val His
        275                 280                 285

Ala Leu Ser Ile Leu Val Ser Thr Phe His His Gly Lys Ile Pro Ser
    290                 295                 300

Ala Ile Asp Gln Arg Thr Phe Glu Glu Tyr Thr Glu Arg Thr Asn Phe
305                 310                 315                 320

Glu Arg Pro Leu Thr Ser Gly Val Ala Tyr Ala Leu Lys Val Pro His
                325                 330                 335

Ser Glu Arg Glu Lys Phe Glu Lys Glu His Gly Trp Ala Ile Lys Lys
            340                 345                 350

Met Glu Thr Glu Asp Gln Thr Val Val Gln Asp Cys Val Pro Glu Asn
        355                 360                 365
```

```
Phe Asp Pro Ala Pro Ile Gln Asp Glu Tyr Ala Pro Val Ile Phe Ala
    370                 375                 380

Gln Glu Thr Val Ser His Ile Val Ser Val Asp Met Met Ser Gly Glu
385                 390                 395                 400

Glu Asp Arg Glu Asn Ile Leu Arg Ala Arg Ala Ser Gly Lys Gly Val
                405                 410                 415

Leu Thr Ser Pro Phe Lys Leu Leu Lys Ser Asn His Leu Gly Val Val
                420                 425                 430

Leu Thr Phe Ala Val Tyr Asp Thr Ser Leu Pro Pro Asp Ala Thr Glu
            435                 440                 445

Glu Gln Arg Val Glu Ala Thr Ile Gly Tyr Leu Gly Ala Ser Tyr Asp
450                 455                 460

Met Pro Ser Leu Val Glu Lys Leu Leu His Gln Leu Ala Ser Lys Gln
465                 470                 475                 480

Thr Ile Ala Val Asp Val Tyr Asp Thr Thr Asn Thr Ser Gly Leu Ile
                485                 490                 495

Lys Met Tyr Gly Ser Glu Ile Gly Asp Ile Ser Glu Gln His Ile Ser
            500                 505                 510

Ser Leu Asp Phe Gly Asp Pro Ser Arg Asn His Glu Met His Cys Arg
        515                 520                 525

Phe Lys His Lys Leu Pro Ile Pro Trp Thr Ala Ile Thr Pro Ser Ile
    530                 535                 540

Leu Val Leu Val Ile Thr Phe Phe Val Gly Tyr Ile Leu Tyr Glu Ala
545                 550                 555                 560

Ile Asn Arg Ile Ala Thr Val Glu Glu Asp Cys Gln Lys Met Arg Glu
                565                 570                 575

Leu Lys Ala Arg Ala Glu Ala Ala Asp Ile Ala Lys Ser Gln Phe Leu
                580                 585                 590

Ala Thr Val Ser His Glu Ile Arg Thr Pro Met Asn Gly Val Leu Gly
            595                 600                 605

Met Leu Lys Met Leu Met Asp Thr Asp Leu Asp Ala Lys Gln Met Asp
610                 615                 620

Tyr Ala Gln Thr Ala His Gly Ser Gly Lys Asp Leu Thr Ser Leu Ile
625                 630                 635                 640

Asn Glu Val Leu Asp Gln Ala Lys Ile Glu Ser Gly Arg Leu Glu Leu
                645                 650                 655

Glu Asn Val Pro Phe Asp Met Arg Phe Ile Leu Asp Asn Val Ser Ser
                660                 665                 670

Leu Leu Ser Gly Lys Ala Asn Glu Lys Gly Ile Glu Leu Ala Val Tyr
            675                 680                 685

Val Ser Ser Gln Val Pro Asp Val Val Gly Asp Pro Ser Arg Phe
690                 695                 700

Arg Gln Ile Ile Thr Asn Leu Val Gly Asn Ser Ile Lys Phe Thr Gln
705                 710                 715                 720

Glu Arg Gly His Ile Phe Ile Ser Val His Leu Ala Asp Glu Val Lys
                725                 730                 735

Glu Pro Leu Thr Ile Glu Asp Ala Val Leu Lys Gln Arg Leu Ala Leu
            740                 745                 750

Gly Cys Ser Glu Ser Gly Glu Thr Val Ser Gly Phe Pro Ala Val Asn
        755                 760                 765

Ala Trp Gly Ser Trp Lys Asn Phe Lys Thr Cys Tyr Ser Thr Glu Ser
    770                 775                 780

Gln Asn Ser Asp Gln Ile Lys Leu Leu Val Thr Val Glu Asp Thr Gly
```

```
            785                 790                 795                 800
Val Gly Ile Pro Val Asp Ala Gln Gly Arg Ile Phe Thr Pro Phe Met
                    805                 810                 815

Gln Ala Asp Ser Ser Thr Ser Arg Thr Tyr Gly Gly Thr Gly Ile Gly
                820                 825                 830

Leu Ser Ile Ser Lys Arg Leu Val Glu Leu Met Gln Gly Glu Met Gly
                835                 840                 845

Phe Val Ser Glu Pro Gly Ile Gly Ser Thr Ser Phe Thr Gly Val
850                 855                 860

Phe Gly Lys Ala Glu Thr Asn Thr Ser Ile Thr Lys Leu Glu Arg Phe
865                 870                 875                 880

Asp Leu Ala Ile Gln Glu Phe Thr Gly Leu Arg Ala Leu Val Ile Asp
                885                 890                 895

Asn Arg Asn Ile Arg Ala Glu Val Thr Arg Tyr Glu Leu Arg Arg Leu
                900                 905                 910

Gly Ile Ser Ala Asp Ile Val Ser Ser Leu Arg Met Ala Cys Thr Cys
                915                 920                 925

Cys Ile Ser Lys Leu Glu Asn Leu Ala Met Ile Leu Ile Asp Lys Asp
                930                 935                 940

Ala Trp Asn Lys Glu Glu Phe Ser Val Leu Asp Glu Leu Phe Thr Arg
945                 950                 955                 960

Ser Lys Val Thr Phe Thr Arg Val Pro Lys Ile Phe Leu Leu Ala Thr
                965                 970                 975

Ser Ala Thr Leu Thr Glu Arg Ser Glu Met Lys Ser Thr Gly Leu Ile
                980                 985                 990

Asp Glu Val Val Ile Lys Pro Leu Arg Met Ser Val Leu Ile Cys Cys
                995                 1000                1005

Leu Gln Glu Thr Leu Val Asn Gly Lys Lys Arg Gln Pro Asn Arg
        1010                1015                1020

Gln Arg Arg Asn Leu Gly His Leu Leu Arg Glu Lys Gln Ile Leu
        1025                1030                1035

Val Val Asp Asp Asn Leu Val Asn Arg Arg Val Ala Glu Gly Ala
        1040                1045                1050

Leu Lys Lys Tyr Gly Ala Ile Val Thr Cys Val Glu Ser Gly Lys
        1055                1060                1065

Ala Ala Leu Ala Met Leu Lys Pro Pro His Asn Phe Asp Ala Cys
        1070                1075                1080

Phe Met Asp Leu Gln Met Pro Glu Met Asp Gly Phe Glu Ala Thr
        1085                1090                1095

Arg Arg Val Arg Glu Leu Glu Arg Glu Ile Asn Lys Lys Ile Ala
        1100                1105                1110

Ser Gly Glu Val Ser Ala Glu Met Phe Cys Lys Phe Ser Ser Trp
        1115                1120                1125

His Val Pro Ile Leu Ala Met Thr Ala Asp Val Ile Gln Ala Thr
        1130                1135                1140

His Glu Glu Cys Met Lys Cys Gly Met Asp Gly Tyr Val Ser Lys
        1145                1150                1155

Pro Phe Glu Glu Glu Val Leu Tyr Thr Ala Val Ala Arg Phe Phe
        1160                1165                1170

Glu Pro Cys
        1175

<210> SEQ ID NO 2
```

```
<211> LENGTH: 1036
<212> TYPE: PRT
<213> ORGANISM: Arabidopsis thaliana

<400> SEQUENCE: 2
```

| | | | | | | | | | | | | | | |
|---|---|---|---|---|---|---|---|---|---|---|---|---|---|---|
| Met | Ser | Leu | Phe | His | Val | Leu | Gly | Phe | Gly | Val | Lys | Ile | Gly | His | Leu |
| 1 | | | | 5 | | | | | 10 | | | | | 15 | |

| Phe | Trp | Met | Leu | Cys | Cys | Trp | Phe | Val | Ser | Trp | Phe | Val | Asp | Asn | Gly |
|---|---|---|---|---|---|---|---|---|---|---|---|---|---|---|---|
| | | | 20 | | | | | 25 | | | | | 30 | | |

| Ile | Glu | Asp | Lys | Ser | Gly | Leu | Leu | Val | Gly | Ser | Val | Gly | Asp | Leu | Glu |
|---|---|---|---|---|---|---|---|---|---|---|---|---|---|---|---|
| | | | 35 | | | | | 40 | | | | | 45 | | |

| Lys | Thr | Lys | Met | Thr | Thr | Leu | Lys | Lys | Lys | Asn | Lys | Met | Trp | Phe | Trp |
|---|---|---|---|---|---|---|---|---|---|---|---|---|---|---|---|
| | 50 | | | | | 55 | | | | | 60 | | | | |

| Asn | Lys | Ile | Ser | Ser | Ser | Gly | Leu | Lys | Ile | Pro | Ser | Phe | Ser | Tyr | Gln |
|---|---|---|---|---|---|---|---|---|---|---|---|---|---|---|---|
| 65 | | | | | 70 | | | | | 75 | | | | | 80 |

| Phe | Leu | Gly | Ser | Val | Lys | Phe | Asn | Lys | Ala | Trp | Trp | Arg | Lys | Leu | Val |
|---|---|---|---|---|---|---|---|---|---|---|---|---|---|---|---|
| | | | | 85 | | | | | 90 | | | | | 95 | |

| Val | Val | Trp | Val | Val | Phe | Trp | Val | Leu | Val | Ser | Ile | Trp | Thr | Phe | Trp |
|---|---|---|---|---|---|---|---|---|---|---|---|---|---|---|---|
| | | | | 100 | | | | | 105 | | | | | 110 | |

| Tyr | Phe | Ser | Ser | Gln | Ala | Met | Glu | Lys | Arg | Lys | Glu | Thr | Leu | Ala | Ser |
|---|---|---|---|---|---|---|---|---|---|---|---|---|---|---|---|
| | | | 115 | | | | | 120 | | | | | 125 | | |

| Met | Cys | Asp | Glu | Arg | Ala | Arg | Met | Leu | Gln | Asp | Gln | Phe | Asn | Val | Ser |
|---|---|---|---|---|---|---|---|---|---|---|---|---|---|---|---|
| | 130 | | | | | 135 | | | | | 140 | | | | |

| Met | Asn | His | Val | Gln | Ala | Met | Ser | Ile | Leu | Ile | Ser | Thr | Phe | His | His |
|---|---|---|---|---|---|---|---|---|---|---|---|---|---|---|---|
| 145 | | | | | 150 | | | | | 155 | | | | | 160 |

| Gly | Lys | Ile | Pro | Ser | Ala | Ile | Asp | Gln | Arg | Thr | Phe | Ser | Glu | Tyr | Thr |
|---|---|---|---|---|---|---|---|---|---|---|---|---|---|---|---|
| | | | | 165 | | | | | 170 | | | | | 175 | |

| Asp | Arg | Ile | Ser | Phe | Glu | Arg | Pro | Leu | Thr | Ser | Gly | Val | Ala | Tyr | Ala |
|---|---|---|---|---|---|---|---|---|---|---|---|---|---|---|---|
| | | | 180 | | | | | 185 | | | | | 190 | | |

| Met | Arg | Val | Leu | His | Ser | Glu | Arg | Glu | Glu | Phe | Glu | Arg | Gln | Gln | Gly |
|---|---|---|---|---|---|---|---|---|---|---|---|---|---|---|---|
| | | 195 | | | | | 200 | | | | | 205 | | | |

| Trp | Thr | Ile | Arg | Lys | Met | Tyr | Ser | Leu | Glu | Gln | Asn | Pro | Val | His | Lys |
|---|---|---|---|---|---|---|---|---|---|---|---|---|---|---|---|
| | 210 | | | | | 215 | | | | | 220 | | | | |

| Asp | Asp | Tyr | Asp | Leu | Glu | Ala | Leu | Glu | Pro | Ser | Pro | Val | Gln | Glu | Glu |
|---|---|---|---|---|---|---|---|---|---|---|---|---|---|---|---|
| 225 | | | | | 230 | | | | | 235 | | | | | 240 |

| Tyr | Ala | Pro | Val | Ile | Phe | Ala | Gln | Asp | Thr | Val | Ser | His | Val | Val | Ser |
|---|---|---|---|---|---|---|---|---|---|---|---|---|---|---|---|
| | | | | 245 | | | | | 250 | | | | | 255 | |

| Leu | Asp | Met | Leu | Ser | Gly | Lys | Glu | Asp | Arg | Glu | Asn | Val | Leu | Arg | Ala |
|---|---|---|---|---|---|---|---|---|---|---|---|---|---|---|---|
| | | | 260 | | | | | 265 | | | | | 270 | | |

| Arg | Ser | Ser | Gly | Lys | Gly | Val | Leu | Thr | Ala | Pro | Phe | Pro | Leu | Ile | Lys |
|---|---|---|---|---|---|---|---|---|---|---|---|---|---|---|---|
| | | 275 | | | | | 280 | | | | | 285 | | | |

| Thr | Asn | Arg | Leu | Gly | Val | Ile | Leu | Thr | Phe | Ala | Val | Tyr | Lys | Arg | Asp |
|---|---|---|---|---|---|---|---|---|---|---|---|---|---|---|---|
| | 290 | | | | | 295 | | | | | 300 | | | | |

| Leu | Pro | Ser | Asn | Ala | Thr | Pro | Lys | Glu | Arg | Ile | Glu | Ala | Thr | Asn | Gly |
|---|---|---|---|---|---|---|---|---|---|---|---|---|---|---|---|
| 305 | | | | | 310 | | | | | 315 | | | | | 320 |

| Tyr | Leu | Gly | Gly | Val | Phe | Asp | Ile | Glu | Ser | Leu | Val | Glu | Asn | Leu | Leu |
|---|---|---|---|---|---|---|---|---|---|---|---|---|---|---|---|
| | | | | 325 | | | | | 330 | | | | | 335 | |

| Gln | Gln | Leu | Ala | Ser | Lys | Gln | Thr | Ile | Leu | Val | Asn | Val | Tyr | Asp | Ile |
|---|---|---|---|---|---|---|---|---|---|---|---|---|---|---|---|
| | | | 340 | | | | | 345 | | | | | 350 | | |

| Thr | Asn | His | Ser | Gln | Pro | Ile | Ser | Met | Tyr | Gly | Thr | Asn | Val | Ser | Ala |
|---|---|---|---|---|---|---|---|---|---|---|---|---|---|---|---|
| | | | 355 | | | | | 360 | | | | | 365 | | |

| Asp | Gly | Leu | Glu | Arg | Val | Ser | Pro | Leu | Ile | Phe | Gly | Asp | Pro | Leu | Arg |
|---|---|---|---|---|---|---|---|---|---|---|---|---|---|---|---|
| | 370 | | | | | 375 | | | | | 380 | | | | |

| Lys | His | Glu | Met | Arg | Cys | Arg | Phe | Lys | Gln | Lys | Pro | Pro | Trp | Pro | Val |

```
            385                 390                 395                 400
        Leu Ser Met Val Thr Ser Phe Gly Ile Leu Val Ile Ala Leu Leu Val
                        405                 410                 415

Ala His Ile Ile His Ala Thr Val Ser Arg Ile His Lys Val Glu Glu
                        420                 425                 430

Asp Cys Asp Lys Met Lys Gln Leu Lys Lys Ala Glu Ala Ala Asp
                        435                 440                 445

Val Ala Lys Ser Gln Phe Leu Ala Thr Val Ser His Glu Ile Arg Thr
                450                 455                 460

Pro Met Asn Gly Val Leu Gly Met Leu His Met Leu Met Asp Thr Glu
        465                 470                 475                 480

Leu Asp Val Thr Gln Gln Asp Tyr Val Arg Thr Ala Gln Ala Ser Gly
                        485                 490                 495

Lys Ala Leu Val Ser Leu Ile Asn Glu Val Leu Asp Gln Ala Lys Ile
                        500                 505                 510

Glu Ser Gly Lys Leu Glu Leu Glu Glu Val Arg Phe Asp Leu Arg Gly
                        515                 520                 525

Ile Leu Asp Asp Val Leu Ser Leu Phe Ser Ser Lys Ser Gln Gln Lys
                        530                 535                 540

Gly Val Glu Leu Ala Val Tyr Ile Ser Asp Arg Val Pro Asp Met Leu
        545                 550                 555                 560

Ile Gly Asp Pro Gly Arg Phe Arg Gln Ile Leu Thr Asn Leu Met Gly
                        565                 570                 575

Asn Ser Ile Lys Phe Thr Glu Lys Gly His Ile Phe Val Thr Val His
                        580                 585                 590

Leu Val Asp Glu Leu Phe Glu Ser Ile Asp Gly Glu Thr Ala Ser Ser
                        595                 600                 605

Pro Glu Ser Thr Leu Ser Gly Leu Pro Val Ala Asp Arg Gln Arg Ser
                        610                 615                 620

Trp Glu Asn Phe Lys Ala Phe Ser Ser Asn Gly His Arg Ser Phe Glu
        625                 630                 635                 640

Pro Ser Pro Pro Asp Ile Asn Leu Ile Val Ser Val Glu Asp Thr Gly
                        645                 650                 655

Val Gly Ile Pro Val Glu Ala Gln Ser Arg Ile Phe Thr Pro Phe Met
                        660                 665                 670

Gln Val Gly Pro Ser Ile Ser Arg Thr His Gly Gly Thr Gly Ile Gly
                        675                 680                 685

Leu Ser Ile Ser Lys Cys Leu Val Gly Leu Met Lys Gly Glu Ile Gly
                        690                 695                 700

Phe Ser Ser Thr Pro Lys Val Gly Ser Thr Phe Thr Phe Thr Ala Val
        705                 710                 715                 720

Phe Ser Asn Gly Met Gln Pro Ala Glu Arg Lys Asn Asp Asn Gln
                        725                 730                 735

Pro Ile Phe Ser Glu Phe Arg Gly Met Lys Ala Val Val Val Asp His
                        740                 745                 750

Arg Pro Ala Arg Ala Lys Val Ser Trp Tyr His Phe Gln Arg Leu Gly
                        755                 760                 765

Ile Arg Val Glu Val Val Pro Arg Val Glu Gln Ala Leu His Tyr Leu
                        770                 775                 780

Lys Ile Gly Thr Thr Thr Val Asn Met Ile Leu Ile Glu Gln Glu Ile
        785                 790                 795                 800

Trp Asn Arg Glu Ala Asp Asp Phe Ile Lys Lys Leu Gln Lys Asp Pro
                        805                 810                 815
```

```
Leu Phe Leu Ser Pro Lys Leu Ile Leu Leu Ala Asn Ser Val Glu Ser
                820                 825                 830

Ser Ile Ser Glu Ala Leu Cys Thr Gly Ile Asp Pro Ile Val Ile
            835                 840                 845

Val Lys Pro Leu Arg Ala Ser Met Leu Ala Ala Thr Leu Gln Arg Gly
850                 855                 860

Leu Gly Ile Gly Ile Arg Glu Pro Pro Gln His Lys Gly Pro Pro Ala
865                 870                 875                 880

Leu Ile Leu Arg Asn Leu Leu Gly Arg Lys Ile Leu Ile Val Asp
                885                 890                 895

Asp Asn Asn Val Asn Leu Arg Val Ala Ala Gly Ala Leu Lys Lys Tyr
            900                 905                 910

Gly Ala Asp Val Val Cys Ala Glu Ser Gly Ile Lys Ala Ile Ser Leu
            915                 920                 925

Leu Lys Pro Pro His Glu Phe Asp Ala Cys Phe Met Asp Ile Gln Met
            930                 935                 940

Pro Glu Met Asp Gly Phe Glu Ala Thr Arg Arg Ile Arg Asp Met Glu
945                 950                 955                 960

Glu Glu Met Asn Lys Arg Ile Lys Asn Gly Glu Ala Leu Ile Val Glu
                965                 970                 975

Asn Gly Asn Lys Thr Ser Trp His Leu Pro Val Leu Ala Met Thr Ala
            980                 985                 990

Asp Val Ile Gln Ala Thr His Glu  Glu Cys Leu Lys Cys  Gly Met Asp
            995                  1000                1005

Gly Tyr  Val Ser Lys Pro  Phe Glu Ala Glu Gln  Leu Tyr Arg Glu
    1010                 1015                 1020

Val Ser  Arg Phe Phe Asn Ser  Pro Ser Asp Thr Glu  Ser
    1025                 1030                 1035

<210> SEQ ID NO 3
<211> LENGTH: 4595
<212> TYPE: DNA
<213> ORGANISM: Arabidopsis thaliana

<400> SEQUENCE: 3
atgtctataa cttgtgagct cttgaatctt acttcaaaga aagctaagaa gtcgtcgagc      60
agtgacaaga aatggctaaa gaagcctctc ttcttcctga ttttgtgtgg ctctttggta     120
attgttttgg ttatgttctt acggttaggt agaagtcaga aggaggagac agattcttgt     180
aatggagaag agaaagtgtt gtatagacat caaaatgtca caagaagtga gattcatgat     240
ttggtctctt tgttctctga ttcagatcag gtaattgcat gaattgactt gtatttgttg     300
aaattgagct tttgaatacg caccagattt gccttaaagt gtaacagttt ctctgtattt     360
gttgtaggta acatcctttg aatgtcataa ggaatcaagc cctggaatgt ggacaaacta     420
tggtattaca tgttccctga gtgtgcgttc tgataaacaa gagactagag gcttccctg      480 gaatcttggc ttaggacatt ctatctcatc aacatcttgt atgtgtggta atcttgaacc     540
ggtaagataa tattcgattc gacaacatgt gaaggaaatg ctttaagatt tggtgtttag     600
ctagttctca caaagtttta ttgtgaatgt gtttggttat gagtagattt tacagcaacc     660
tgaaaacctt gaggaagaaa accatgaaga agggctggag cagggtttgt catcgtattt     720
aagaaatgca tggtggtgtc taatccttgg tgtgttagtg tgccataaga tttatgtatc     780
tcattctaaa gcacgaggtg agaggaaaga gaaagtacat ctgcaagagg ctttagctcc     840
```

```
aaagaagcag caacaacgtg ctcagacttc ttctagaggg gctggaagat ggaggaagaa    900
tatccttctc cttggtattt taggaggagt ttccttctct gtttggtggt tttgggacac    960
taatgaggag atcataatga aaaggaggga gactttggca acatgtgtg acgaacgagc    1020
acgtgtttta caagatcagt tcaatgttag cttgaaccat gttcatgcct tgtctattct    1080
tgtatctaca tttcatcatg gtaaaatccc atctgccatt gatcaggtga tgttttttc    1140
ttactgctaa atacattttg tgtctcaagt ttatgtttaa atcatcaact tctgttacat    1200
ttacagagaa catttgaaga atatactgag agaacaaact ttgagaggcc acttactagt    1260
ggtgtagcgt atgctttgaa agtcccacac tcagaaagag agaaatttga aaaggagcat    1320
ggatgggcaa taaagaaaat ggaaactgag gaccagacag ttgtacaaga ttgtgttcct    1380
gaaactttg atcccgcacc gattcaagac gaatacgcgc cagttatatt tgctcaagaa    1440
actgtttccc atattgtatc ggtcgacatg atgtctggag aagtcagtaa cgtctaaaag    1500
tttcttgaac tattttgcca aaccaatgtc cttaaaagag aattcaaaag tctaactatt    1560
ttgcaggaag accgtgaaaa catcttacgg gcaagggcat caggaaaagg agtgttaaca    1620
tctccattta agcttcttaa gtcaaatcat cttggtgttg tgttgaccct tgctgtctat    1680
gacacgagcc taccgcctga tgctacagaa gaacagcgtg ttgaagcaac tattgggtac    1740
tacttctact aaaatgatt ctaggactga agaaattgaa cctatgtaac aaagaatgat    1800
ctctggacca gaaaatatta ataagataca cttaaaaaca ggtaccttgg tgcatcatat    1860
gatatgccat cgctggtgga gaaacttctt caccaacttg ccagcaaaca gacaattgct    1920
gtggatgttt acgacacaac taacacttca ggtctaataa aatgtatgg ctcagaaatt    1980
ggggatataa gtgagcagca tataagtagc cttgattttg gtgatccatc aaggaaccat    2040
gagatgcatt gcaggttagt tagctctaac tgttatggta catttttata agatatgttt    2100
cacttctctg ttttctgaag tatgaaagtg gcattttca tttacaggtt taagcataaa    2160
cttcccattc cctggacagc gataacaccg tcgatcttag ttctggttat tactttttt    2220
gttggttata ttttatatga agccatcaac cgaattgcga cagttgaaga ggattgtcag    2280
aagatgaggg aactcaaagc tcgtgctgag gccgctgaca ttgcaaagtc acaggtgatc    2340
tttgtgaatc atatagtctc aaaagcttta cttgttttt cactgaaatg cttcttattt    2400
tgcagttcct agcaactgtt tctcatgaga tacggactcc gatgaatgga gttttaggta    2460
cttttctac ttatccttgg tcaatattgc atgttctctt aaaatcagct gaaacgttta    2520
agcattttgt tacaggaatg ctgaaaatgc tgatggacac cgatcttgat gcgaagcaga    2580
tggactatgc gcaaactgct catggcagtg ggaaggatct tacatcacta ataaatgagg    2640
ttcttgatca ggcaaagatt gaatccggaa ggctcgagct tgaaaatgtg cctttgata    2700
tgcgttttat tcttgataat gtttcatctc tcctctctgg caaggcaaat gaaaaaggaa    2760
ttgaggtata attataaact gcatgacctt ctactttctt aatgttttca tatggcaaac    2820
aaattccata tgtaatgaaa tgttgacttc ttgttacagt tggccgttta tgtttctagt    2880
caagttcctg atgttgtagt cggtgatccg agtcggttcc ggcagatcat tacaaacctg    2940
gttgaaact caatcaaagt aatttactcc ttacttctta cagaacaaca ggcttcacga    3000
atctctacta ttacagtact catttgttat ttacttaata acagttcaca caggaaaggg    3060
gacacatatt tatctcagtg caccttgcag atgaggtaaa ggagcctctt actattgaag    3120
acgcagtgct aaaacagcga ctagcttag gatgcagcga gtccggtgag acagttagcg    3180
ggtttcctgc ggtaaatgca tggggaagct ggaagaattt caagacatgt tacagtactg    3240
```

```
agagtcagaa ttctgatcaa atcaaattgc tagttacagt ggaggacact ggagttggca    3300
tacctgtgga tgcacaaggc cgaatcttca cccttttat gcaagccgac agttccacat     3360
cgcggactta tggtggaact ggcataggtt tgagtataag caaacgtttg gttgaactca    3420
tgcaaggaga gatggggttt gtgagtgagc ccgggatagg cagtactttt tcatttactg    3480
gagttttcgg gaaagcagaa acaaatacgt cgattactaa gctggaacga ttcgatctag    3540
ctattcagga gtttacagga ttgagagcat tagttattga taacagaaac attagagcag    3600
aggtcaccag gtacgaactt cggagactgg gaatatctgc agacattgtt tcaagtctga    3660
gaatggcatg cacttgttgt atcaggtact ttacgtacat tagtgtctgt ctgtctttag    3720
agattatagt gagttcacta aaagcgtttt attgttctgg aatctttgca gcaaattaga    3780
aaatttggct atgattctaa tagacaaaga cgcctggaac aaggaagaat ttcagtact     3840 tgacgagttg tttacccgaa gcaaagtaac ctttacaaga gtcccaaaga ttttctttt    3900 ggcaacttct gcaactctta ctgagcgcag tgagatgaag tctactgtc tcatcgatga     3960 ggtggtgata aagcctcttc ggatgagtgt cttaatatgt tgcttgcaag aaacccttgt    4020
caatggcaag aagaggcaac cgaacagaca gcgaagaaat cttggacact tgctaagaga    4080
aaaacagatt ctggttgtgg atgataatct tgtgaacaga cgagttgcag aaggtgcact    4140
taagaaatat ggagctattg ttacatgcgt tgagagtggc aaagctgcat ggcaatgct     4200 taagccgcct cataacttcg atgcttgctt catggatctc cagatgcctg aaatggatgg    4260
gtagataact attttcaat cttatctctt cagcttgttc atttcttgga tgtcgtcctt     4320 ggtaactta taatttttg cgcagatttg aagcgacaag gagagtccgt gagctggaga     4380
gggaaatcaa taagaaaata gcttctggag aagtttcagc tgaaatgttc tgtaaattta    4440
gtagttggca cgtcccgata ttagcaatga cagcagatgt tattcaggct actcatgaag    4500
aatgcatgaa atgtggaatg gatggttatg tatcaaaacc gtttgaagag gaagtgctct    4560
acacagcggt agcaagattc tttgaacctt gttaa                              4595
```

<210> SEQ ID NO 4
<211> LENGTH: 4248
<212> TYPE: DNA
<213> ORGANISM: Arabidopsis thaliana

<400> SEQUENCE: 4

```
atgagtctgt tccatgtgct agggtttggt gtcaagattg gcatctctt ctggatgcta      60 tgctgctggt ttgtttcttg gttcgttgat aatgggatcg aggacaagtc tggtctttta    120
gttggctctg tcggtgatct tgagaagact aagatgacta cgttgaagaa gaagaacaag    180
atgtggttct ggaataagat ctctagcagc ggactcaaga tcccgagttt ctcttatcag    240
tttcttggct ctgttaaatt caacaaggcg tggtggagga gcttgtggt ggtttgggtt     300 gtcttctggg tcttggtctc tatttggacg ttttggtact ttagctcgca agctatggag    360
aagaggaaag agacgctagc tagtatgtgt gatgagagag ctcgtatgct gcaggatcag    420
ttcaacgtta gcatgaatca tgttcaagcc atgtctatct tgatctcaac cttccaccat    480
ggcaagattc cttctgctat cgatcaggta ttctcgattc cgcatcttct tgtcttctaa    540 tctgttttgga ttgatgcctg agatctagtc ttgcttgtag tacataagtt gttcctacgg   600
tgtagtatat gaacggtcct tggatgatgg tagctttttt cattcaactt gctctcgaat    660
ttcagttagg atttacaatt ttgctgattg ttgcttacag tctttgtatt tagctaacac    720
```

```
ttggtagctt gattcctatc ttcttgagta ttagtgaaca gtaactaaca ttaagaagct      780
ttgtgtagag aacattctca gagtacactg atagaatttc ctttgagagg cctcttacta      840
gcggggtagc ttatgctatg agggtgctcc attcagagag ggaagagttc gagaggcaac      900
aaggttggac tattaggaag atgtattctc ttgaacaaaa cccagttcac aaggatgact      960
atgacctgga agctttggaa ccatccctg tccaagaaga gtacgctcca gtcatctttg      1020
ctcaggacac tgtttctcac gttgtttctc tcgatatgct gtctgggaaa gtaagcttct      1080
ttactggttc taattttact gtttttatgt aatttactat catggtctac actcactacc      1140
gggcgaatcc tgccgacatg gctagttcat atttcaatct cggcttaccg attaagttgt      1200
tttgatcatt ttatttaaag tttagagcac tgttttaact gatacttatt ctcactcaat      1260
tcctcttgat aggaagatcg tgaaaacgtt ttgcgggcca ggagttcagg taaaggggtt      1320
ttgacagctc ctttcccatt gataaagaca aatagacttg gggtgatcct gacatttgca      1380
gtgtacaaga gagatctccc ctccaatgca acgccaaaag agagaattga ggctactaac      1440
gggtgtgtag cataggcgtc taaataaata ataacgcata agttttacaa cattattttt      1500
gctcattcat ctcttttgat gcccctgaag gtatctcggg ggagtgtttg acattgagtc      1560
cctggtagaa aacttgcttc aacagctggc tagcaagcaa acgattcttg tcaatgtgta      1620
cgatatcacc aatcactctc aaccgattag catgtatggt acaaatgtgt cggctgatgg      1680 gttgaacgt gttagtccac taatctttgg cgatccattg agaaagcatg agatgcgttg      1740
caggtacttg cagttggcac atacatatgt ctgtaatttc ttcttgtttg caagaatcca      1800
ggtgctaaca ttttgttgtg agcttcttcc tctttgtaga tttaagcaga aaccaccatg      1860
gccagtgcta tcaatggtga catcattcgg tatccttgtg attgcgttac ttgttgcaca      1920
tataatccac gcaaccgtta gtcgaataca caaagttgaa gaagattgtg ataaaatgaa      1980
gcagctcaag aaaaaggctg aagcagcaga tgttgcaaag tcacaggtaa atacatcatc      2040
ctcagttgat aaatttccac agcatattaa acttttctatg acagagagaa gagttgtaat      2100 ctaactttt tttatgcagt tccttgccac tgtttcacat gaaatcagaa ctccaatgaa      2160
tggtgttcta ggtgagtatc gaaatggcca ctatgttgcc tccttctctc acctatgccc      2220
atgaatattt tctgaagaac aaacttaacc aaatattctc atgttgactt tgatctgggg      2280
tgtaggaatg ttgcatatgc ttatggacac agagttagat gttacgcaac aggattatgt      2340
taggaccgca caggcaagtg aaaagctttt agtctcgcta ataaatgagg ttttggacca      2400
agcaaagatt gaatctggaa agcttgaact tgaggaggtg cggtttgatt tgagaggaat      2460
attagatgat gtcctgtcac tcttctctag caagtcccaa caaagggggg tggaggtaac      2520
ttactatatg atcctgcaaag caagggttgt aactgatagc aagtcttct tactgatttt       2580 ttgagtgttg ctgatgaacg cagttggcag tatacatatc tgatcgtgtt ccagatatgt      2640
taattggtga tcctgggagg tttcgacaaa tactcacaaa tcttatgggt aattccatta      2700
aggtaaactt ttttattatg ttttttttctg accattcctt gcatccgagt tgatcaacgg      2760
agctgatcat ttatatatat tctggcagtt cactgagaaa ggacacatct ttgtaactgt      2820
tcatttggtg gatgagctat ttgaatctat cgatggagag acagcatcat ctccggaaag      2880
tacactgagt gggcttccag ttgcagaccg gcagaggagc tgggaaaact ttaaagcttt      2940
cagctccaac gggcatcgga gctttgaacc atctccccct gatataaacc taatcgtctc      3000
agttgaggat actggcgtag ggatccctgt agaagcgcag tcccgtattt ttacgccttt      3060
catgcaagtc ggaccatcca tatccaggac gcatggaggc acaggaattg gacttagcat      3120
```

```
aagcaaatgt ctagttggac tgatgaaggg agaaattgga ttctcgagta ctcccaaggt    3180
tgggtccaca ttcacattta ctgctgtatt ttccaatggg atgcaaccag ctgaaagaaa    3240
gaatgacaac aaccagccca tattctcgga attccggggc atgaaagctg tggttgtgga    3300
ccataggcct gcaagggcaa aagtctcgtg gtaccatttt cagcgtcttg gaattcgagt    3360
cgaagtagtt ccacgtgttg aacaggctct acattatctg aagattggta ctaccactgt    3420
gaatatgata ctcatagagc aagaaatatg gaatagggaa gcagatgatt tcattaaaaa    3480
gctacagaaa gaccctcttt tcctttctcc taagttgatt ttgttagcaa actcagtaga    3540
atcgtcaata tcagaggctt tatgcaccgg tatagatcct ccaatagtga tagtgaaacc    3600
attgagggcg agtatgctag cagcaacttt gcagagggga ttgggtattg aatcagaga    3660 accacctcaa cacaagggac ctcctgcttt gattctcagg aatcttctcc ttggtagaaa    3720 aatttttaatc gtggatgata acaacgtaaa cctcagagtg gcagcgggag ctctgaaaaa    3780
gtacggagct gatgtggtct gcgctgagag tgggataaag gcaatctcat tgcttaagcc    3840
acctcacgag tttgatgctt gcttcatgga cattcagatg ccagaaatgg atgggtatgc    3900
ctgattggta tactagtttt tttgaaaagt tcgaaatatg taataagaaa attgaaatgt    3960
ttttctgccc tgtctttctg cagatttgaa gctacaagga gaatacgaga tatggaagag    4020
gagatgaaca agagaataaa gaatggggag gctttgatag tagagaacgg taacaaaaca    4080
agctggcatc ttccggtatt agcaatgacg gcagatgtga tccaagcaac gcatgaggaa    4140
tgtctgaagt gtggaatgga tgggtatgta tcaaaaccat ttgaagcaga gcagctgtac    4200
agggaagttt ctcgcttttt caattcgcct tcagatacag aatcataa                4248
```

<210> SEQ ID NO 5
<211> LENGTH: 50
<212> TYPE: PRT
<213> ORGANISM: Arabidopsis thaliana

<400> SEQUENCE: 5

Glu Ile Gly Asp Ile Ser Glu Gln His Ile Ser Ser Leu Asp Phe Gly
1               5                   10                  15

Asp Pro Ser Arg Asn His Glu Met His Cys Arg Phe Lys His Lys Leu
            20                  25                  30

Pro Ile Pro Trp Thr Ala Ile Thr Pro Ser Ile Leu Val Leu Val Ile
        35                  40                  45

Thr Phe
    50

<210> SEQ ID NO 6
<211> LENGTH: 50
<212> TYPE: PRT
<213> ORGANISM: Arabidopsis thaliana

<400> SEQUENCE: 6

Ser Phe Glu Arg Pro Leu Thr Ser Gly Val Ala Tyr Ala Met Arg Val
1               5                   10                  15

Leu His Ser Glu Arg Glu Glu Phe Glu Arg Gln Gln Gly Trp Thr Ile
            20                  25                  30

Arg Lys Met Tyr Ser Leu Glu Gln Asn Pro Val His Lys Asp Asp Tyr
        35                  40                  45

Asp Leu
    50